US005378808A

United States Patent [19]

D'Andrea et al.

[11] Patent Number: 5,378,808

[45] Date of Patent: Jan. 3, 1995

[54] RECOMBINANT ERYTHROPOIETIN RECEPTOR PROTEIN

[75] Inventors: Alan D'Andrea, Winchester; Gordon G. Wong, Brookline; Simon S. Jones, Somerville, all of Mass.

[73] Assignee: Genetics Institute, Inc., Cambridge, Mass.

[21] Appl. No.: 75,069

[22] Filed: Jun. 10, 1993

Related U.S. Application Data

[60] Division of Ser. No. 678,877, Mar. 25, 1991, Pat. No. 5,278,065, which is a continuation-in-part of Ser. No. 306,503, Feb. 3, 1989, abandoned.

[51] Int. Cl.[6] .............................................. C07K 13/00
[52] U.S. Cl. .................................... 530/350; 435/69.1
[58] Field of Search ........................ 435/69.1; 530/350

[56] References Cited

FOREIGN PATENT DOCUMENTS

WO90/08822 8/1990 WIPO .

OTHER PUBLICATIONS

Jones et al., Blood 76:31-35 (1990).
D'Andrea et al., Cell 57:277-285 (1989).
Kuramochi et al., Mol. Biol. 216:567-575 (1990).
Sawyer et al., PNAS 84:3690-3694 (1987).
Todokoro et al., PNAS 84:4126-4130 (1987).
Powell et al., PNAS 83:6465-6469 (1986).
McDonald et al., Mol. Cell. Biol. 6:842-848 (1986).
Sims et al., Science 241: 585-588 (1988).
Seed et al., PNAS 84:3365-3369 (1987).
Winkelmann et al., Blood 76(1):24-30 (1990).

*Primary Examiner*—Garnette D. Draper
*Assistant Examiner*—John P. Ulm
*Attorney, Agent, or Firm*—Thomas J. DesRosier; Patricia A. McDaniels; Scott A. Brown

[57] ABSTRACT

The invention described encompasses an isolated DNA sequence encoding all or a portion thereof of a cell surface receptor murine and human erythropoietin (hereinafter EPO-R), along with the isolated polypeptide expressed by the DNA sequence (i.e., isolated EPO-R). The invention also encompasses host cells containing the above-described DNA sequence, preferably, host cells which express the polypeptide encoded by the DNA sequence (EPO-R) at a significantly higher level than that produced by normal red blood cell precursors. The invention further encompasses DNA sequences encoding secreted forms of the human EPO-R and polypeptides corresponding thereto. The EPO-receptor in all of the disclosed forms can be used as models for designing drugs or in pharmaceutical compositions for treating anemias.

3 Claims, 12 Drawing Sheets

MEL EPO Receptor cDNA Sequence

```
             11                  28          40          52                      76
tgagcttcct  gaagctaggg  ctgcatc ATG GAC AAA CTC AGG GTG CCC CTC TGG CCT CGG GTA GGC CCC CTC TGT CTC CTA CTT GCT GGG GCA CGG TGG
                                M   D   K   L   R   V   P   L   W   P   R   V   G   P   L   C   L   L   L   A   G   A   A   W
↓
100                             124                             148                             172
GCA CCT TCA CCC AGC CTC CCG GAC CCC AAG TTT GAG AGC AAA GCG GCC CTG CTG GCA TCC CGG GGC TCC GAA GAA CTT CTG TGC TTC ACC CAA CGC
A   P   S   P   S   L   P   D   P   K   F   E   S   K   A   A   L   L   A   S   R   G   S   E   E   L   L   C   F   T   Q   R

196                             220                             244                             268
TTG GAA GAC TTG GTG TGT TTC TGG GAG GAA GCG GCG AGC TCC GGG ATG GAC TTC|AAC TAC AGC|TTC TCA TAC CAG CTC GAG GGT GAG TCA CGA AAG
L   E   D   L   V   C   F   W   E   E   A   A   S   S   G   M   D   F  |N   Y   S  |F   S   Y   Q   L   E   G   E   S   R   K

292                             316                             340                             368
TCA TGT AGC CTG CAC CAG GCT CCC ACC GTC CGC GGC TCC GTG CGT TTC TGG TGT TCA CTG CCA ACA GCG GAC ACA TCG AGT TTT GTG CCG CTG GAG
S   C   S   L   H   Q   A   P   T   V   R   G   S   V   R   F   W   C   S   L   P   T   A   D   T   S   S   F   V   P   L   E

388                             412                             436                             460
CTG CAG GTG ACG GAG GCG TCC GGT TCT CCT CGC TAT CAC CGC ATC ATC CAT ATC AAT GAA GTA GTG CTC CTG GAC GCC CCC GCG GGG CTG CTG GCG
L   Q   V   T   E   A   S   G   S   P   R   Y   H   R   I   I   H   I   N   E   V   V   L   L   D   A   P   A   G   L   L   A

484                             508                             532                             556
CGC CGG GCA GAA GAG GGC AGC CAC GTG GTG CTG CGC TGG CTG CCA CCT CCT GGA GCA CCT ATG ACC ACC CAC ATC CGA TAT GAA GTG GAC GTG TCG
R   R   A   E   E   G   S   H   V   V   L   R   W   L   P   P   P   G   A   P   M   T   T   H   I   R   Y   E   V   D   V   S

580                             604                             628                             652
GCA GGC AAC CGG GCA GGA GGG ACA CAA AGG GTG GAG GTC CTG GAA GGC CGC ACT GAG TGT GTT CTG AGC AAC CTG CGG GGC GGG ACG CGC TAC ACC
A   G   N   R   A   G   G   T   Q   R   V   E   V   L   E   G   R   T   E   C   V   L   S   N   L   R   G   G   T   R   Y   T

676                             700                             724                             748
TTC GCT GTT CGA GCG CGC ATG GCC GAG CCG AGC TTC AGC GGA TTC TGG AGT GCC TGG TCT GAG CCC GCG TCA CTA CTG ACC GCT AGC GAC CTG GAC
F   A   V   R   A   R   M   A   E   P   S   F   S   G   F   W   S   A   W   S   E   P   A   S   L   L   T   A   S   D   L   D
```

MEL EPO-R cDNA RESTRICTION MAP

Figure 2

MEL EPO Receptor cDNA Sequence

```
           11                   28                  40                  52                                  76
tgagcttcct gaagctaggg ctgcatc ATG GAC AAA CTC AGG GTG CCC CTC TGG CCT CGG GTA GGC CCC CTC TGT CTC CTA CTT GCT GGG GCA CGG TGG
                              M   D   K   L   R   V   P   L   W   P   R   V   G   P   L   C   L   L   L   A   G   A   A   W
↓
100                             124                             148                             172
GCA CCT TCA CCC AGC CTC CCG GAC CCC AAG TTT GAG AGC AAA GCG GCC CTG CTG GCA TCC CGG GGC TCC GAA GAA CTT CTG TGC TTC ACC CAA CGC
A   P   S   P   S   L   P   D   P   K   F   E   S   K   A   A   L   L   A   S   R   G   S   E   E   L   L   C   F   T   Q   R

196                             220                             244                             268
TTG GAA GAC TTG GTG TGT TTC TGG GAG GAA GCG GCG AGC TCC GGG ATG GAC TTC[AAC TAC AGC]TTC TCA TAC CAG CTC GAG GGT GAG TCA CGA AAG
L   E   D   L   V   C   F   W   E   E   A   A   S   S   G   M   D   F  [N   Y   S  ]F   S   Y   Q   L   E   G   E   S   R   K

292                             316                             340                             368
TCA TGT AGC CTG CAC CAG GCT CCC ACC GTC CGC GGC TCC GTG CGT TTC TGG TGT TCA CTG CCA ACA GCG GAC ACA TCG AGT TTT GTG CCG CTG GAG
S   C   S   L   H   Q   A   P   T   V   R   G   S   V   R   F   W   C   S   L   P   T   A   D   T   S   S   F   V   P   L   E

388                             412                             436                             460
CTG CAG GTG ACG GAG GCG TCC GGT TCT CCT CGC TAT CAC CGC ATC ATC CAT ATC AAT GAA GTA GTG CTC CTG GAC GCC CCC GCG GGG CTG CTG GCG
L   Q   V   T   E   A   S   G   S   P   R   Y   H   R   I   I   H   I   N   E   V   V   L   L   D   A   P   A   G   L   L   A

484                             508                             532                             556
CGC CGG GCA GAA GAG GGC AGC CAC GTG GTG CTG CGC TGG CTG CCA CCT CCT GGA GCA CCT ATG ACC ACC CAC ATC CGA TAT GAA GTG GAC GTG TCG
R   R   A   E   E   G   S   H   V   V   L   R   W   L   P   P   P   G   A   P   M   T   T   H   I   R   Y   E   V   D   V   S

580                             604                             628                             652
GCA GGC AAC CGG GCA GGA GGG ACA CAA AGG GTG GAG GTC CTG GAA GGC CGC ACT GAG TGT GTT CTG AGC AAC CTG CGG GGC GGG ACG CGC TAC ACC
A   G   N   R   A   G   G   T   Q   R   V   E   V   L   E   G   R   T   E   C   V   L   S   N   L   R   G   G   T   R   Y   T

676                             700                             724                             748
TTC GCT GTT CGA GCG CGC ATG GCC GAG CCG AGC TTC AGC GGA TTC TGG AGT GCC TGG TCT GAG CCC GCG TCA CTA CTG ACC GCT AGC GAC CTG GAC
F   A   V   R   A   R   M   A   E   P   S   F   S   G   F   W   S   A   W   S   E   P   A   S   L   L   T   A   S   D   L   D
```

Figure 2A

```
772                                 796                                                     820                                     844
CCT CTC ATC TTG ACG CTG TCT CTC ATT CTG GTC CTC ATC TCG CTG TTG CTG ACG GTT CTG GCC CTG CTG TCC CAC CGC CGG ACT CTG CAG CAG AAG
P   L   I   L   T   L   S   L   I   L   V   L   I   S   L   L   L   T   V   L   A   L   L   S   H   R   R   T   L   Q   Q   K
868                                 892                                                     916                                     940
ATC TGG CCT GGC ATC CCA AGC CCA GAG AGC GAG TTT GAG GGT CTC TTC ACC ACC CAC AAG GGT AAC TTC CAG CTG TGG CTG CTG CAG CGT GAT GGT
I   W   P   G   I   P   S   P   E   S   E   F   E   G   L   F   T   T   H   K   G   N   F   Q   L   W   L   L   Q   R   D   G
964                                 988                                                     1012                                    1036
TGT CTG TGG TGG AGC CCG GGC AGC TCC TTC CCT GAG GAT CCA CCT GCC CAC CTA GAG GTC CTC TCA GAG CCA CGC TGG GCA GTG ACT CAG GCT GGG
C   L   W   W   S   P   G   S   S   F   P   E   D   P   P   A   H   L   E   V   L   S   E   P   R   W   A   V   T   Q   A   G
1060                                1084                                                    1108                                    1132
GAC CCA GGG GCA GAT GAT GAG GGG CCC TTA CTG GAG CCG GTG GGC AGT GAG CAT GCC CAG GAC ACC TAC TTG GTA TTG GAT AAG TGG TTG CTG CCC
D   P   G   A   D   D   E   G   P   L   L   E   P   C   G   S   E   H   A   Q   D   T   Y   L   V   L   D   K   W   L   L   P
1156                            1180                                                        1204                                    1228
CGG ACC CCA TGC AGT GAG AAC CTC TCA GGG CCT GGG GGC AGT GTG GAC CCT GTG ACT ATG GAT GAA GCT TCA GAA ACA TCT TCC TGC CCG TCT GAC
R   T   P   C   S   E   N   L   S   G   P   G   G   S   V   D   P   V   T   M   D   E   A   S   E   T   S   S   C   P   S   D
1252                                1276                                                    1300                                    1324            *
TTG GCC TCA AAG CCC AGG CCA GAG GGC ACC TCA CCT TCC AGC TTT GAG TAC ACC ATC CTG GAC CCC AGC TCT CAG CTC CTG TGC CCT CGG GCA CTG
L   A   S   K   P   R   P   E   G   T   S   P   S   S   F   E   Y   T   I   L   D   P   S   S   Q   L   L   C   P   R   A   L
1348                                1372                                                    1396                                    1420
CCT CCC GAG CTA CCT CCC ACT CCA CCT CAC TTG AAG TAC CTA TAC CTT GTG GTG TCC GAT TCT GGC ATC TCA ACA GAT TAC AGT TCG GGG GGC TCT
P   P   E   L   P   P   T   P   P   H   L   K   Y   L   Y   L   V   V   S   D   S   G   I   S   T   D   Y   S   S   G   G   S
1444                                1468                                                    1492                                    1516
CAG GGA GTC CAC GGG GAC TCA TCT GAT GGC CCC TAC TCC CAC CCC TAT GAG AAC AGC CTT GTC CCA GAC TCA GAG CCT CTG CAT CCC GGC TAT GTG
Q   G   V   H   G   D   S   S   D   G   P   Y   S   H   P   Y   E   N   S   L   V   P   D   S   E   P   L   H   P   G   Y   V
1540                            1562                  1582                       1602                   1622                  1642
GCC TGC TCC TAG gactccagcc tacaacgtct tgaacgggat tggtgaagcc ata cttaaag tcagagctga ccttggccct ctgagcagga agagacagcc ttgcaatgtt
A   C   S

                1662                            1682                    1702                        1722
aagattaaga gttatctgtc tgtatataga  aatatatata tatatcgatt tttctacc tt  gaaaaaaaaa aaaaaaaaaa aaaaaaaaaa
```

Binding of Iodinated EPO to MEL Cells

FIGURE 9

-100 -80 -60 -40
TCAGCTGCGTCCGGCGGAGGCAGCTGCTGACCCAGCTGTGGACTGTGCCGGGGGCGGGGGACGGAGGGGC

-20 0 20
AGGAGCCCTGGGCTCCCCGTGGCGGGGGCTGTATCATGGACCACCTCGGGGCGTCCCTCTGGCCCCAGGT
M D H L G A S L W P Q V 12

40 60 80 100
CGGCTCCCTTTGTCTCCTGCTCGCTGGGGCCGCCTGGGCGCCCCCGCCTAACCTCCCGGACCCCAAGTTC
G S L C L L L A G A A W A P P P N L P D P K F 35

120 140 160
GAGAGCAAAGCGGCCTTGCTGGCGGCCCGGGGGCCCGAAGAGCTTCTGTGCTTCACCGAGCGGTTGGAGG
E S K A A L L A A R G P E E L L C F T E R L E D 59

180 200 220 A 240
ACTTGGTGTGTTTCTGGGAGGAAGCGGCGAGCGCTGGGGTGGGCCCGGGCAACTACAGCTTCTCCTACCA
L V C F W E E A A S A G V G P G N Y S F S Y Q 82

260 280 300
GCTCGAGGATGAGCCATGGAAGCTGTGTCGCCTGCACCAGGCTCCCACGGCTCGTGGTGCGGTGCGCTTC
L E D E P W K L C R L H Q A P T A R G A V R F 105

320 340 360 380
TGGTGTTCGCTGCCTACAGCCGACACGTCGAGCTTCGTGCCCCTAGAGTTGCGCGTCACAGCAGCCTCCG
W C S L P T A D T S S F V P L E L R V T A A S G 129

400 420 440
GCGCTCCGCGATATCACCGTGTCATCCACATCAATGAAGTAGTGCTCCTAGACGCCCCCGTGGGGCTGGT
A P R Y H R V I H I N E V V L L D A P V G L V 152

460 480 500 520
GGCGCGGTTGGCTGACGAGAGCGGCCACGTAGTGTTGCGCTGGCTCCCGCCGCCTGAGACACCCATGACG
A R L A D E S G H V V L R W L P P P E T P M T 175

540 560 580
TCTCACATCCGCTACGAGGTGGACGTCTCGGCCGGCAACGGCGCAGGGAGCGTACAGAGGGTGGAGATCC
S H I R Y E V D V S A G N G A G S V Q R V E I L 199

600 620 640 660
TGGAGGGCCGCACCGAGTGTGTGCTGAGCAACCTGCGGGGCCGGACGCGCTACACCTTCGCCGTCCGCGC
E G R T E C V L S N L R G R T R Y T F A V R A 222

680 700 720
GCGTATGGCTGAGCCGAGCTTCGGCGGCTTCTGGAGCGCCTGGTCGGAGCCTGTGTCGCTGCTGACGCCT
R M A E P S F G G F W S A W S E P V S L L T P 245

740 760 780 800
AGCGACCTGGACCCCCTCATCCTGACGCTCTCCCTCATCCTCGTGGTCATCCTGGTGCTGCTGACCGTGC
S D L D P L I L T L S L I L V V I L V L L T V L 269

FIGURE 9A

```
                820  ▽          840                 860
TCGCGCTGCTCTCCCACCGCCGGGCTCTGAAGCAGAAGATCTGGCCTGGCATCCCGAGCCCAGAGAGCGA
 A  L  L] S  H  R  R  A  L  K  Q  K  I  W  P  G  I  P  S  P  E  S  E    292

  880               900           ▽ 920                 940
GTTTGAAGGCCTCTTCACCACCCACAAGGGTAACTTCCAGCTGTGGCTGTACCAGAATGATGGCTGCCTG
 F  E  G  L  F  T  T  H  K  G  N  F  Q  L  W  L  Y  Q  N  D  G  C  L    315

                960                 980                 1000
TGGTGGAGCCCCTGCACCCCCTTCACGGAGGACCCACCTGCTTCCCTGGAAGTCCTCTCAGAGCGCTGCT
W  W  S  P  C  T  P  F  T  E  D  P  P  A  S  L  E  V  L  S  E  R  C  W    339

  1020              1040                1060                1080
GGGGGACGATGCAGGCAGTGGAGCCGGGGACAGATGATGAGGGCCCCCTGCTGGAGCCAGTGGGCAGTGA
 G  T  M  Q  A  V  E  P  G  T  D  D  E  G  P  L  L  E  P  V  G  S  E    362

                1100                1120                1140
GCATGCCCAGGATACCTATCTGGTGCTGGACAAATGGTTGCTGCCCCGGAACCCGCCCAGTGAGGACCTC
 H  A  Q  D  T  Y  L  V  L  D  K  W  L  L  P  R  N  P  P  S  E  D  L    385

  1160              1180                1200                1220
CCAGGGCCTGGTGGCAGTGTGGACATAGTGGCCATGGATGAAGGCTCAGAAGCATCCTCCTGCTCATCTG
P  G  P  G  G  S  V  D  I  V  A  M  D  E  G  S  E  A  S  S  C  S  S  A    409

                1240                1260                1280
CTTTGGCCTCGAAGCCCAGCCCAGAGGGAGCCTCTGCTGCCAGCTTTGAGTACACTATCCTGGACCCCAG
 L  A  S  K  P  S  P  E  G  A  S  A  A  S  F  E  Y  T  I  L  D  P  S    432

  1300              1320                1340                1360
CTCCCAGCTCTTGCGTCCATGGACACTGTGCCCTGAGCTGCCCCCTACCCCACCCCACCTAAAGTACCTG
 S  Q  L  L  R  P  W  T  L  C  P  E  L  P  P  T  P  P  H  L  K  Y  L    455

                1380                1400                1420
TACCTTGTGGTATCTGACTCTGGCATCTCAACTGACTACAGCTCAGGGGACTCCCAGGGAGCCCAAGGGG
Y  L  V  V  S  D  S  G  I  S  T  D  Y  S  S  G  D  S  Q  G  A  Q  G  G    479

  1440              1460                1480                1500
GCTTATCCGATGGCCCCTACTCCAACCCTTATGAGAACAGCCTTATCCCAGCCGCTGAGCCTCTGCCCCC
 L  S  D  G  P  Y  S  N  P  Y  E  N  S  L  I  P  A  A  E  P  L  P  P    502

                1520                1540                1560
CAGCTATGTGGCTTGCTCTTAGGACACCAGGCTGCAGATGATCAGGGATCCAATATGACTCAGAGAACCA
 S  Y  V  A  C  S  *                                                      525

  1580              1600                1620                1640
GTGCAGACTCAAGACTTATGGAACAGGGATGGCGAGGCCTCTCTCAGGAGCAGGGGCATTGCTGATTTTG

                1660                1680                1700
TCTGCCCAATCCATCCTGCTCAGGAAACCACAACCTTGCAGTATTTTTAAATATGTATAGTTTTTTTG
```

FIGURE 10

```
    -710                   -690                   -670                    -650
GGATCCCATCTCTACAAAGAATTTTAAAAATTAGCCAGGTGCAGTGGGAAGATTGCTTCAGTCCAGAGGC

                  -630                  -610                   -590
TGCAGTGAGCTATGATTGTGCCACTGCACTCCAGCCTGGGTGACAGAGCAACACCCTGAGACAGAGAGAG

    -570                   -550                   -530                    -510
AGAGGGGGAAGGAGGGAAGGAGGGAAGGAAGGAAGGAAGGAAGGAAGGAAGGAAGGAAGGAAGGAAGGAA

                  -490                  -470                   -450
GGAAAGGAGAGAGAGAGAGAGAGAGAGAGAGAGAGAGAGAGAGAGAGAGAAAATAATTTTTATTTATTTCCA

    -430                   -410                   -390                    -370
GGCTGGGAAGAGATGCTGATTTCTGCGATAAAATCAGTAGGTACATTTTTTGGAATGTTCGCTATGTGCC

                  -350                  -330                   -310
AGGCTAGATTTTACAGATGAGAAGTCTGAAGCTCAGGTAAGGTAAGTCACCTGTCCAGGGCCACAAAGAA

    -290                   -270                   -250                    -230
AAAAAAAACGTGTGTCTGAAGCCAGAACGGGAGCTGTTGCGGCCCAACTCCCTCCCCTGCCCCCAAGCGG

                  -210                  -190                   -170
CCTCTGGGCTCGGGAAGGGCCCCTGCCTCCTCCCGCCAGGCACTTATCTCTACCCAGGCTGAGTGCTGGC

    -150                   -130                   -110                    -90
CCCGCCCCCTCGGGGATCTGCCACTTAGAGGCGCCTGGTCGGGAAGGGCCTGGTCAGCTGCGTCCGGCGG

                  -70                   -50                    -30
AGGCAGCTGCTGACCCAGCTGTGGACTGTGCCGGGGGCGGGGACGGAGGGGCAGGAGCCCTGGGCTCCC

    -10                    10                     30                      50
CGTGGCGGGGGCTGTATCATGGACCACCTCGGGGCGTCCCTCTGGCCCCAGGTCGGCTCCCTTTGTCTCC
                    M  D  H  L  G  A  S  L  W  P  Q  V  G  S  L  C  L  L   18

TGCTCGCTGGGGCC
 L  A  G  A    22
```

RECOMBINANT ERYTHROPOIETIN RECEPTOR PROTEIN

This application is a divisional of allowed U.S. Ser. No. 07/678,877 filed Mar. 25, 1991 now U.S. Pat No. 5,278,865; which is a continuation in part of U.S. Ser. No. 07/306,503 filed Feb. 3, 1989 now abandoned.

DESCRIPTION

GOVERNMENT SUPPORT

Work described herein was supported by funding from the National Institutes of Health.

BACKGROUND

Erythropoiesis, the production of red blood cells, occurs in the bone marrow under the physiological control of the hormone erythropoietin (EPO). Erythropoietin is a 34,000 dalton glycoprotein hormone which is synthesized in the kidney, circulates in the plasma, and is excreted in the urine. In response to changes in the level of oxygen in the blood and tissues, erythropoietin appears to stimulate both proliferation and differentiation of immature erythroblasts. It functions as a growth factor, stimulating the mitotic activity of erythroid progenitor cells, such as erythrocyte burst forming and colony-forming units. It also acts as a differentiation factor, triggering transformation of an erythrocyte colony-forming-unit into a proerythroblast (Erslev, A., New Eng. J. Med. 316:101-103 (1987)).

Normally, erythropoietin is found in very low concentrations in bodily fluids. However, under conditions of hypoxia, when oxygen transport to erythrocytes in reduced, the concentration of erythropoietin in the blood stream increases. For example, in patients suffering from aplastic anemia, there is an abnormally high concentration of erythropoietin in the urine. a specific activity of at least 160,000 IU per absorbance unit at 280 nanometers. (Hewick, et al., U.S. Pat. No. 4,677,195). The DNA sequence encoding erythropoietin was purified and cloned to produce synthetic polypeptides with the same biochemical and immunological properties. (Lin, U.S. Pat. No. 4,703,008). A recombinant erythropoietin molecule with oligosaccharides identical to those of the natural material has also been produced. (Sasaki, H. et al., J. Biol. Chem. 262:12059-12076 (1987)).

Despite the availability of purified recombinant erythropoietin, little is known concerning the mechanism of erythropoietin-induced erythroblast proliferation and differentiation. The specific interaction of erythropoietin with immature red blood cell progenitors remains to be characterized. This is due, at least in part, to the small number of surface erythropoietin receptor molecules on normal erythroblasts and the erythroleukemia cell line. (Krantz, S. B. and E. Goldwasser, Proc. Natl. Acad. Sci. U.S.A. 81:7574-7578 (1984); Branch D. R. et al., Blood 69:1782-1785 (1987); Mayeux, P. et al., FEBS Letters 211:229-233 (1987); Mufson, R. A. and T. G. Gesner, Blood 69:1485-1490 (1987); Sakaguchi, M. et al., Biochem. Biophys. Res. Commun. 146:7-12 (1987); Sawyer, S. T. et al., Proc. Natl. Acad. Sci. U.S.A. 84:3690-3694 (1987); Sawyer, S. T. et al., J. Biol. Chem. 262:5554-5562 (1987); Todokoro, K. et al., Proc. Natl. Acad. Sci. U.S.A. 84:4126-4130 (1988)).

Cross-linked complexes between radioiodinated erythropoietin and cell surface proteins suggest that the receptor is made up of two polypeptides, one of which has a molecular weight of 85,000 Daltons and the other of 100,000 Daltons. More recently, the two crosslinked complexes have been subjected to V8 protease digestion, suggesting the two EPO-receptor polypeptides have identical peptide fragments and therefore may be products of the same or very similar genes (Sawyer, S. T. et al., J. Biol. Chem. 266:13343-13347 (1988)). Most cell surface binding studies, however, have revealed a single class of binding sites, averaging 300 to 600 per cell surface, with a $K_d$ of approximately 800 pM (Sawyer, S. T. et al., Proc. Natl. Acad, Sci. U.S.A. 84:3690-3694 (1987)). EPO-responsive splenic erythroblasts, prepared from mice injected with the anemic strain (FVA) of the Friend leukemia virus, demonstrate a high and a low affinity binding site with dissociation constants of 100 pM and 800 pM, respectively (Sawyer, S. T. et al., J. Biol. Chem. 262:5554-5562 (1987)).

Mouse erythroleukemia cells, although unresponsive to erythropoietin, are a readily available source of EPO receptor. They have a single class of EPO receptor with fewer than 1000 sites per cell and a dissociation constant of $2\times10^{-10}$ M. (Mayeux, P. et al., J. Biol. Chem. 262:13985-13990 (1987)); D'Andrea, A. et al., Cell 57:277-285 (1989)). Crosslinking studies with radioiodinated erythropoietin reveal two putative receptor polypeptides with molecular weights of 100,000 and 85,000 Daltons.

Knowledge of the mechanism of action of erythropoietin would be of great clinical benefit in treating a number of diseases in which the erythropoietin receptor may be dysfunctional. For instance, it is believed that the erythropoietin receptor is dysfunctional in individuals with Diamond Blackfan anemia, which is a congenital anemia in which the infant is profoundly anemic and requires red blood cell transfusions and steroid treatments. In primary proliferative polycythemia (polycythemia vera), the erythropoietin receptor may be dysfunctional but, in this case, it appears to be hyperactive with EPO levels at or below normal (Murphy, S., *Polycythemia Vera In: Hematology 4th Edition* (1990)), resulting in a disease characterized in adults by an excess of red blood cell mass. Indeed, mature erythroid precursors (BFU-E) have a greater sensitivity to EPO than more primitive precursors, which have an enhanced sensitivity to IL-3 (Dudley, J. M. et al., Br. J. Haematol. 75:188-194 (1990) and Dai, C. H. et al., J. Clin. Invest. 87:391-396 (1991)). In contrast, secondary polycythemia (erythrocytosis) is caused by elevated levels of EPO, resulting from tissue hypoxia due to decreased oxygen tension in the blood supply or inappropriate EPO production induced by an underlying disease state (Erslev, A. J., *Secondary Polycythemia (Erythrocytosis): Hematology 4th Edition* (1990)). Furthermore, in autoimmune diseases, such as lupus and juvenile rheumatoid arthritis, antibodies to the erythropoietin receptor may account for the anemia associated with these diseases.

SUMMARY OF THE INVENTION

The invention described encompasses an isolated DNA sequence encoding all or a portion of a cell surface receptor for erythropoietin (hereinafter EPO-R), or the functional equivalent thereof, as well as the isolated polypeptide encoded by the DNA sequence (referred to as isolated EPO-R). The invention also encompasses host cells containing the above-described DNA sequence, methods of producing the encoded EPO-R and methods of treatment which make use of the encoded EPO-R, antibodies specific for EPO-R or other products which enhance or inhibit EPO-R activity.

The DNA sequence encoding EPO-R and the encoded polypeptide have several utilities. For example, the DNA sequence encoding all or a portion of murine EPO-R can be used to define the active EPO/EPO-R complex and to explain the presence of two complexes formed by crosslinking radioiodinated EPO to the EPO-R, where the latter is generated from a single cDNA species. It can be used to define those proteins which interact with the EPO/EPO-R complex to transduce a proliferative and maturation signal to EPO sensitive cells. In addition, because of its EPO-binding ability, the murine or human polypeptide (EPO-R) can be used to purify EPO. For example, the receptor can be used directly in batch form or can be immobilized in a column.

Polypeptide (EPO-R) can be used as an immunogen for the production of antibodies or antibody fragments which are specific for EPO-R. These antibodies can be produced using standard somatic cell fusion techniques (Kohler and Milstein, Nature 256:52–53 (1975)). A therapeutically effective amount of the polypeptide or a portion thereof, e.g. a secreted form of the receptor, can be used in pharmaceutical compositions for treating individuals who are either hypersensitive to EPO due to dysfunctions in the EPO receptor or proteins involved in the signal transduction pathway, or who have elevated levels of EPO. The understanding and characterization of the erythropoietin receptor may result in the elucidation of the mechanism by which erythropoietin stimulates erythropoiesis. This may advance the study of several human diseases which are believed to be the result of a defective EPO-R.

BRIEF DESCRIPTION OF THE DRAWINGS

FIGS. 2 and 2A is the murine EPO receptor cDNA (clone 190) nucleotide and predicted amino acid sequences. The hydrophobic putative signal peptide and putative transmembrane regions are underlined. The sites of potential asparagine-linked glycosylation are underlined with a dotted line.

FIGS. 9 and 9A is the nucleotide sequence for clone #18 human EPO receptor cDNA. The downward arrow indicates the hypothetical mature amino terminus. The upward arrow indicates the base difference with the PCR clone. Open triangles show the exon boundaries and the underlined sequence is the presumed transmembrane domain.

FIG. 10 is the 5'-untranslated sequence of the human EPO receptor from the genomic clone. The boxes are defined in Example 2.

DETAILED DESCRIPTION OF THE INVENTION

Cloning of the EPO Receptor cDNA

Figure 1:
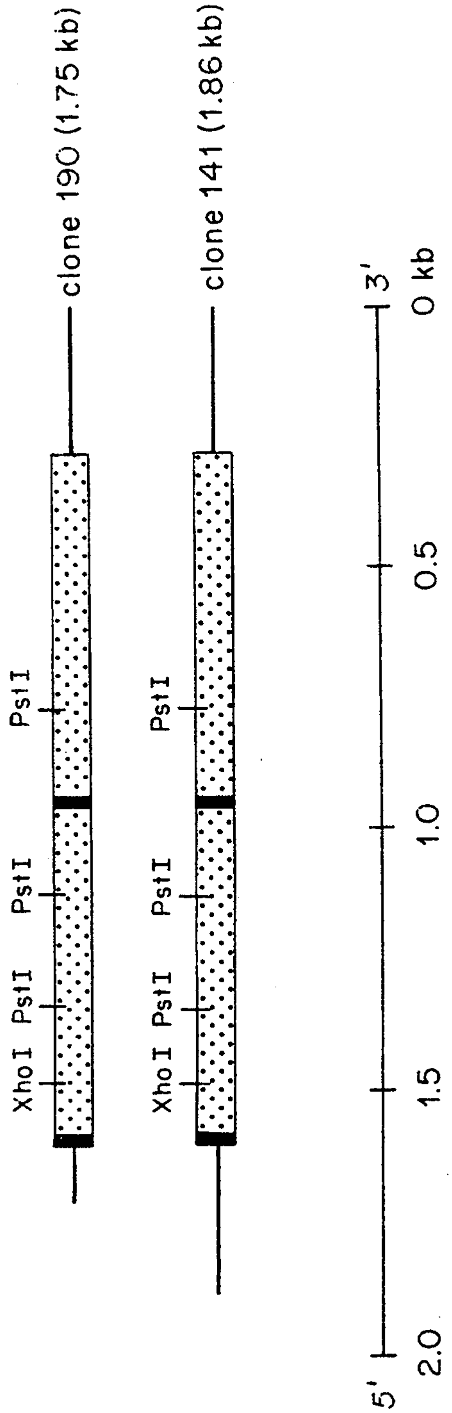
FIG. 1 is a schematic representation and restriction map of two independent cDNA clones of the murine EPO receptor (Murine Erythroleukemia (MEL)) cell erythropoietin receptor cDNA. The black boxes indicate the location of the signal peptide and the transmembrane region. The coding region is shown by an open box.

The present invention relates to DNA encoding an EPO-R of mammalian origin, to the encoded EPO-R and to their use in detecting EPO-R dysfunction, as well as in treating individuals in whom such dysfunction occurs. The following is a description of cloning and expression of DNA encoding EPO-R, of the characterization/assessment of EPO-R and of uses of EPO-R or related materials for diagnostic and therapeutic purposes.

This invention encompasses DNAs which comprise the nucleotide sequences depicted in FIGS. 2, 2A, 9, 9A and 10 or which otherwise encode the mature peptide sequences depicted therein. This invention further encompasses DNA which is capable of hybridizing to the aforesaid DNA, especially under stringent conditions, and which encodes, on expression, preferably in mammalian host cells, EPO receptor protein, or a portion thereof, as can be readily determined, e.g., by methods disclosed in detail hereinafter. This invention further encompasses cDNAs encoding secreted human EPO receptor protein and the corresponding secreted human EPO receptor protein, and methods of making and using the secreted human EPO receptor protein.

In many embodiments, such EPO receptor-encoding DNA is covalently linked to heterologous DNA, i.e., DNA from sources other than that of the EPO receptor-encoding DNA. Typically such constructs comprise plasmids or vectors containing the DNA of this invention linked with vector DNA and various genetic elements advantageous for selection, transcription control, amplification, etc. as described in greater detail below.

A detailed description of methods for obtaining DNAs of this invention is provided in the examples.

Murine clone 190 inserted within the cloning site of mammalian expression vector pXM (described in Yang, et al. (1986)) has been deposited with the American Type Culture Collection as ATCC No. 40546. Two cloned human genomic EPO receptor DNA fragments inserted within the cloning site of a lambda phage vector have also been deposited under ATCC No. 40547 and ATCC No. 40548.

DNAs of this invention are preferably expressed in mammalian host cells, although bacterial, yeast and insect cell expression may be readily effected using purely conventional methods and materials.

Eukaryotic, preferably mammalian, expression vectors into which the DNAs of this invention may be inserted (with or without synthetic linkers, as desired or necessary) may be synthesized by techniques well known to those skilled in this art. The components of the vectors such as the bacterial replicons, selection genes, enhancers, promoters, and the like may be obtained from natural sources or synthesized by known procedures. See Kaufman et al., J. Mol. Biol. 159:601–621 (1982); Kaufman, Proc. Natl. Acad. Sci. 82:689–693 (1985). Eucaryotic expression vectors useful in producing variants of this invention may also contain inducible promoters or comprise inducible expression systems as are known in the art. See e.g., "High Level Inducible Expression of Heterologous Genes", International Application No. PCT/US87/01871, the contents of which are incorporated herein by reference.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese Hamster Ovary) cells are currently considered preferred. Alternatively, the vector DNA may include all or part of the bovine papilloma virus genome (Lusky et al., Cell 36:391–401 (1984)) and be carried in cell lines such as C127 mouse cells as a stable episomal element. Other usable mammalian cell lines include HeLa, COS-1 monkey cells, melanoma cell lines, such as Bowes cells, mouse L-929 cells, 3T3 lines derived from Swiss, Balb-c or NIH mice, BHK or HaK hamster cell lines and the like.

Plasmid pMT2 may be obtained by EcoRI digestion of pMT2-VWF, which has been deposited with the American Type Culture Collection under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods and then ligated to DNAs of this invention. pXM, a derivative of pMT2, may also be used as an alternative to pMT2.

Transformants, preferably of mammalian cells such as COS or CHO cells, containing and capable of expressing the cDNAs of this invention provide cell lines useful for the production of EPO receptor protein. CHO cells, in particular, allow the production, identification and recovery of stably transformed cell lines containing amplified gene copy number of the EPO receptor DNA and expressing recombinant EPO receptor protein in yields permitting recovery thereof from the cell cultures. Suitable transformation, selection, amplification and cell culture methods are conventional in this art.

It should be noted that the presence of EPO receptor protein may be conveniently detected by use of radiolabeled or otherwise labeled EPO protein. EPO protein may be obtained by methods now well known in the art. See e.g. Published International Application No. W 86/03520. In addition, EPO protein is now commercially available.

EPO receptor protein may be recovered from the cell cultures by conventional means, including affinity chromatography using immobilized EPO protein as the affinity reagent, reverse phase HPLC, and other techniques conventional for recovery of membrane bound protein. Genetically engineered cells expressing EPO on the cell membrane can be used to recover the EPO receptor protein.

Thus, this invention provides for the first time EPO receptor protein, preferably human, free or substantially free from other proteins with which it is otherwise associated in nature. Preferably the EPO receptor protein is 90%, and more preferably more than 95% pure on a wt/wt basis from other proteins.

The EPO receptor protein of this invention may be used for the production for the first time of idiotypic or antiidiotypic antibodies to the receptor, whether polyclonal or monoclonal, which antibodies are also encompassed by this invention. Such antibodies may be useful therapeutically in the treatment of anemias.

The EPO receptor protein may also be used as an affinity reagent for the identification (e.g., in EPO assays) or purification of EPO. Each of these uses is based on the binding affinity of EPO for its receptor. In the case of purification of EPO, it should be noted that the murine receptor protein may be as efficient as or better than the corresponding human receptor protein. In the case of assays, it should be noted that the EPO receptor protein may be radiolabeled or may be expressed as a fusion protein with beta-galactosidase, alkaline phosphatase or other enzymatic labels for convenient monitoring. Additionally, it should be noted that truncated forms of the EPO receptor which retain the EPO binding site may also be used for such purposes.

For instance, it should be noted that DNAs of this invention for the first time provide EPO-R modified by deletion of part or preferably all of the region encoding the membrane-spanning protein domain, or modified by deletion of part or all of the region encoding the protein domains preceding (N-terminal to) the extracellular domains of the receptor protein. Expression of such modified DNAs by the methods disclosed herein permit the production of EPO receptor protein variants which retain EPO binding activity but are no longer membrane bound. Such variants may be secreted from the producing cells and recovered from the culture media.

Additionally, it should be noted that EPO receptor proteins of this invention may also be used in the screening of other agents, including modified forms of EPO, which retain EPO receptor binding activity. Binding assays using a desired binding protein, immobilized or not, are well known in the art and may be used for this purpose using an EPO receptor protein of this invention. Compounds found to retain at least about 10%, preferably greater than about 50% or more of the binding activity of human EPO may thus be identified and then secondarily screened in the now well known EPO activity assays, preferably in vivo activity assays. By these means compounds having EPO activity which may be suitable as alternatives to EPO may be identified.

Pharmaceutical compositions containing the secreted form of the EPO receptor of the present invention may be useful in treating such conditions as primary proliferative polycythemia or secondary polycythemia. Such pharmaceutical compositions may also contain pharmaceutically acceptable carriers, diluents, fillers, salts, buffers, stabilizers and/or other materials well known in the art. The term "pharmaceutically acceptable" means a non-toxic material that does not interfere with the effectiveness of the biological activity of the active ingredient(s). The characteristics of the carrier or other material will depend on the route of administration.

Administration of the secreted form of the EPO receptor can be carried out in a variety of conventional ways. Intravenous or subcutaneous administration to the patient is preferred.

Cutaneous or subcutaneous injection may be employed and in that case the secreted form of the EPO receptor will be in the form of pyrogen-free, parenterally acceptable aqueous solutions. The preparation of such parenterally acceptable protein solutions, having due regard to pH, isotonicity, stability, and the like, is within the skill in the art.

Intravenous injection may be employed, wherein the secreted form of the EPO receptor will be in the form of pyrogen-free, parenterally acceptable aqueous solutions. A preferred pharmaceutical composition for intravenous injection should contain, in addition to the secreted form of the EPO receptor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additives known to those of skill in the art.

The amount of secreted form of the EPO receptor in the pharmaceutical composition of the present invention will depend upon the nature and severity of the condition being treated, and on the nature of prior treatments which the patient has undergone. Ultimately, the attending physician will decide the amount of secreted form of the EPO receptor with which to treat each individual patient. It is contemplated that the various pharmaceutical compositions of the present invention should contain about 0.01 μg to about 100 mg of secreted form of the EPO receptor per kg body weight.

The secreted form of the EPO receptor of the present invention can be used for the in vivo treatment of mammals by physicians in a variety of disease conditions. Some of these conditions include primary proliferative polycythemia and secondary polycythemia. In sum, the pharmaceutical methods and compositions of the present invention may be used in the treatment of primary proliferative polycythemia.

In practicing the method of treatment of this invention, a therapeutically effective amount of secreted form of the EPO receptor is administered to a mammal having such a disease state. The term "therapeutically effective amount" means the total amount of each active component of the method or composition that is sufficient to show a meaningful patient benefit, i.e., healing of chronic conditions or increase in rate of healing. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the secreted form of the EPO receptor of this invention is contemplated to be in the range of about 0.01 μg to about 100 mg per kg body weight per application. The duration of intravenous therapy using the pharmaceutical composition of the present invention will vary, depending on the severity of the disease being treated and the condition and potential idiosyncratic response of each individual patient. It is contemplated that the duration of each application of the secreted form of the EPO receptor will be in the range of 12 to 24 hours of continuous intravenous administration. Ultimately the attending physician will decide on the appropriate duration of intravenous therapy using the pharmaceutical composition of the present invention.

Construction of a Murine cDNA Library

A cDNA library from uninduced MEL cells which express the EPO-R was expressed and analyzed as described in Example 1. From uninduced MEL cells, which express approximately 700 receptors per cell surface, a cDNA library was prepared in the mammalian expression vector pXM (Yang, Y. et al., Cell 47:3-10 (1986)). The library contained approximately 800,000 independent clones. These were plated into pools, each with approximately 1000 different recombinant bacterial colonies. Plasmid minipreps were prepared from each pool (Maniatis, T. et al., *Molecular Cloning: A Laboratory Manual*, Cold Spring Harbor Laboratory, Cold Spring Harbor, N.Y. (1982)) and plasmid DNA was transfected in duplicate into COS monolayers by the DEAE dextran method (Sompayrac, L. M. and K. J. Danna, Proc. Natl. Acad. Sci. U.S.A. 78:7575-7578 (1981)).

After 72 hours, at the time of peak heterologous protein synthesis, the uptake of radioiodinated recombinant EPO was measured at 37° C. for 90 minutes. The EPO was internalized by receptor-mediated endocytosis, and a greater signal was achieved than by measuring binding at 4° C. to surface EPO-R's. After uptake, the COS monolayers were washed extensively, and counted in a gamma counter. Under these conditions, background binding of radiolabeled EPO to a 10 centimeter plate of confluent COS cell transfectants was approximately 800 counts per minute. The two positive pools of recombinant plasmids (out of 200 pools, or a total of 200,000 recombinant clones tested), when transfected into COS monolayers, yielded binding of 1200 to 3000 cpm. These two pools of plasmids, numbers 141 and 190, were partitioned into subpools until a single cDNA clone capable of causing COS cells to bind and uptake $^{125}$I-EPO was obtained from each pool. When two micrograms of either of the purified single clones was transfected into COS monolayers, radiolabeled EPO uptake at 37° C. was greater than 200,000 cpm.

Cloning of the Murine EPO Receptor cDNA

Two cDNA clones encoding EPO-R have been isolated from a pXM expression library made from uninduced (MEL) cells and identified by screening COS cell transfectants for binding and uptake of radioiodinated recombinant human erythropoietin. As inferred from the cDNA sequence, the murine EPO-R is a 507 amino acid polypeptide with a single membrane spanning domain. It shows no similarities to known proteins or nucleic acid sequences. Although the MEL cell EPO-R has a single affinity (approximately 240 pM), the EPO-R cDNA, expressed in COS cells, generates both a high affinity receptor (30 pM) and a low affinity receptor (210 pM). The isolation of the two independent cDNA clones from a MEL cell library, when transfected alone into COS cells, encode a functional murine EPO receptor.

Characterization and Sequence of the Murine cDNA

The inserts of the two specific EPO receptor cDNA clones were excised by Kpn digestion and analyzed by agarose gel electrophoresis. Clone 141 had a slightly longer insert (1.9 kb) than clone 190 (1.8 kb). The restriction maps of both clones were identical; clone 141 was 100 bp longer at the 5' terminus (FIG. 1). Pst-digested cDNA fragments from the two clones were subcloned into M13mp18 or M13mp19 vectors and the nucleotide sequence was determined by the chain termination method (Sanger, F. et al., Proc. Natl. Acad. Sci. U.S.A. 74:5463–5467 (1977)). Both strands of the cDNA clones sequenced were shown to be co-linear except for a two base pair deletion at nucleotide position 1333–1335 (FIG. 2, arrow). To further evaluate this discrepancy between the two cDNA clones, the normal mouse structural gene for the EPO-R was cloned and sequenced. The coding region for the normal mouse gene agrees with the cDNA sequence shown for clone 190.

The 1773 base cDNA nucleotide sequence of clone 190, shown in FIG. 2, reveals a single open reading frame of 507 amino acids. The 3' untranslated region extends for an additional 167 bases and ends with a poly(A) tail. The first initiator codon (ATG) in clone 190 is 43 bases from the 5' end. No consensus sequence typical of translation initiation (Kozak, M., Nucl. Acids Res. 15:8125–8148 (1987)) was found in the 5' untranslated region.

Figure 3:
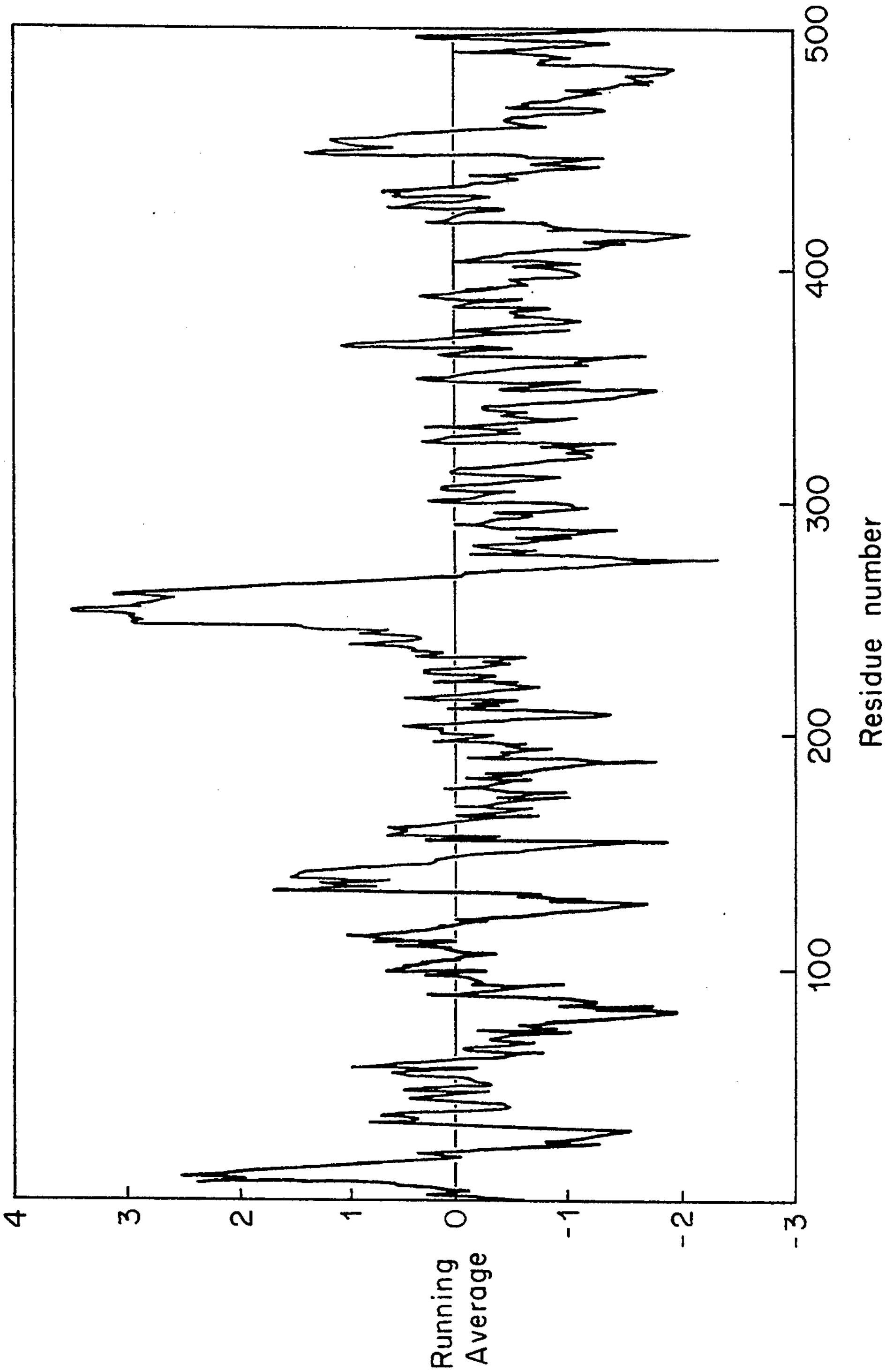
FIG. 3 is a hydropathy plot of the predicted amino acid sequence of murine EPO-receptor by the method of Kyte et al., J. Mol. Biol. 157:105–132 (1982). Positive values represent increased hydrophobicity.

Since the clones were isolated by an expression strategy, the clones are complete, and encode a polypeptide capable of normal processing, cell surface localization, and binding of EPO. Consistent with the assignment of the first ATG as initiator (FIG. 2), there are three stop codons in frame 5' to the first methionine of the predicted amino acid sequence. The N-terminal 24 residues have all of the features of a typical signal sequence. The hydrophobicity plot (Kyte, J. and R. F. Doolittle, J. Mol. Biol. 157:105–132 (1982)) predicts a single 23 amino acid membrane-spanning alpha-helical segment from amino acids 248–271 (FIG. 3). The putative transmembrane region is followed by a sequence of mostly basic residues. This feature is common to the cytosolic face of the membrane-spanning segments of many proteins. This suggests an amino-terminus-exoplasmic-carboxy-terminus-cytoplasmic orientation, or a so-called type I transmembrane protein.

There are two potential sites of N-linked glycosylation, one in the putative extracellular domain and one in the putative cytoplasmic domain. Also, 12% of the amino acids are serine residues and 5% are threonine making extensive O-linked glycosylation a possibility (Russell, D. W. et al., Cell 37:577–585 (1984)). The discrepancy between the sizes of the putative receptor polypeptides, observed by crosslinking studies—85,000 or 100,000 daltons—and the predicted 57,000 mw predicted from the cDNA sequence could be accounted for by glycosylation. Also, there is a high frequency of proline residues (10% of total amino acids), present throughout the sequence, suggesting an absence of alpha-helical secondary structure.

The nucleotide and amino acids sequences revealed no significant homology to any other cloned genes in the Gen bank data base. The deduced amino acid sequence of the EPO receptor reveals several overall features common to other growth factor receptors. The extracellular domain (amino acid 25–248) should contain the EPO binding region. Despite the existence of five cysteine residues within this region, there is no evidence of the conserved disulfide loops characteristic of receptors of the immunoglobulin superfamily (Sims, J. E. et al., Science 241:585–589 (1988)). The intracellular domain (amino acids 272–507) could serve a role in signal transduction. Despite its large size, the cytoplasmic domain has no apparent sequence homology with the catalytic domain of any growth factor receptor known to be a tyrosine kinase (Hanks, S. K. et al., Science 241:42–52 (1988)).

Binding Characteristics of the Recombinant Murine EPO Receptor

Figure 4:
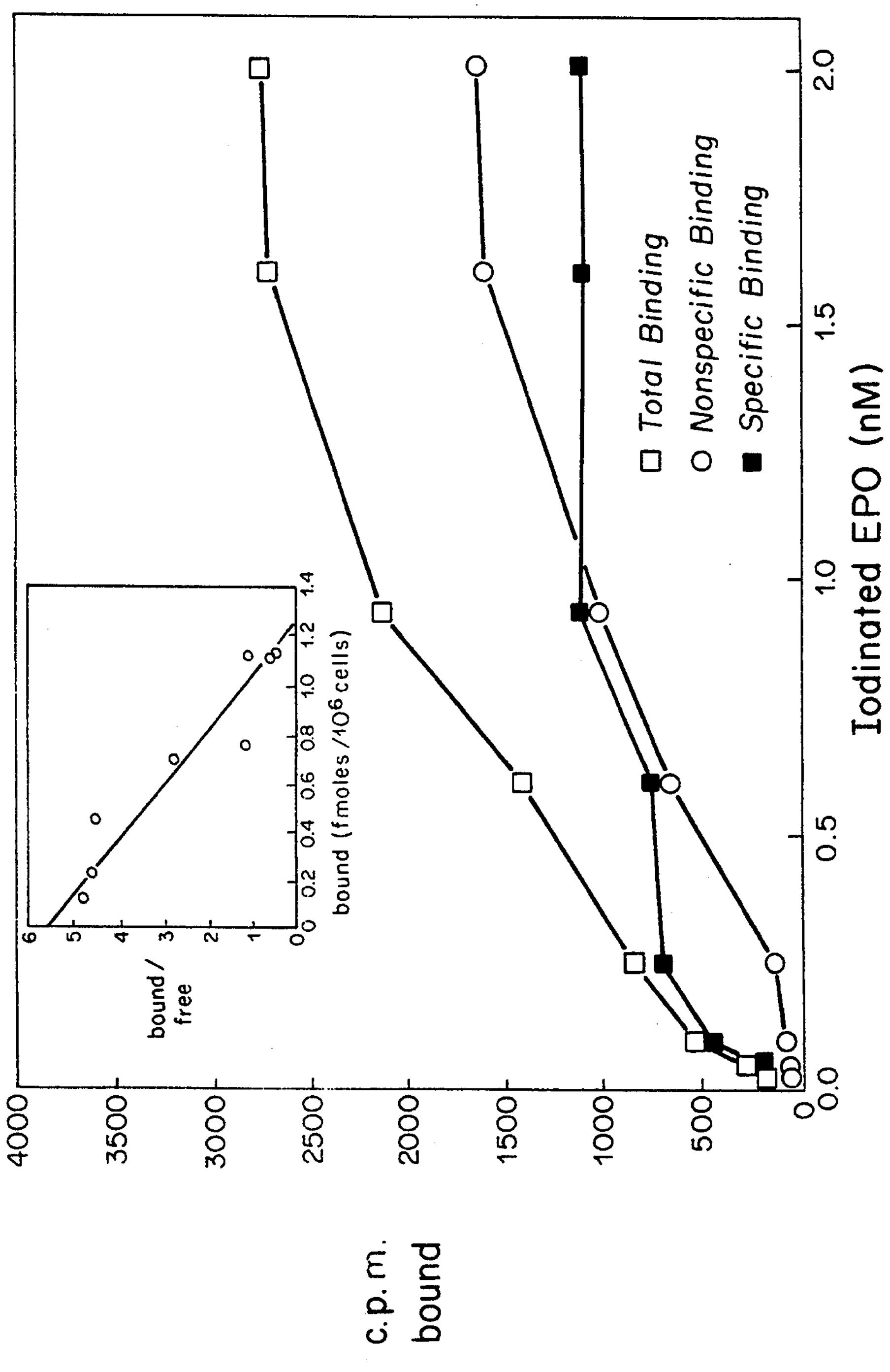
FIG. 4 is a saturation curve showing the binding of iodinated EPO to MEL cells. Non-specific binding was determined by co-incubation with 100 nM of unlabeled EPO. The MEL cells were grown on fibronectin monolayers and were incubated with various concentrations of radioiodinated human EPO for eight hours at 4° C. The specific binding is shown as the difference between total and non-specific binding. The inset is a Scatchard plot of the same data.
Figure 5:
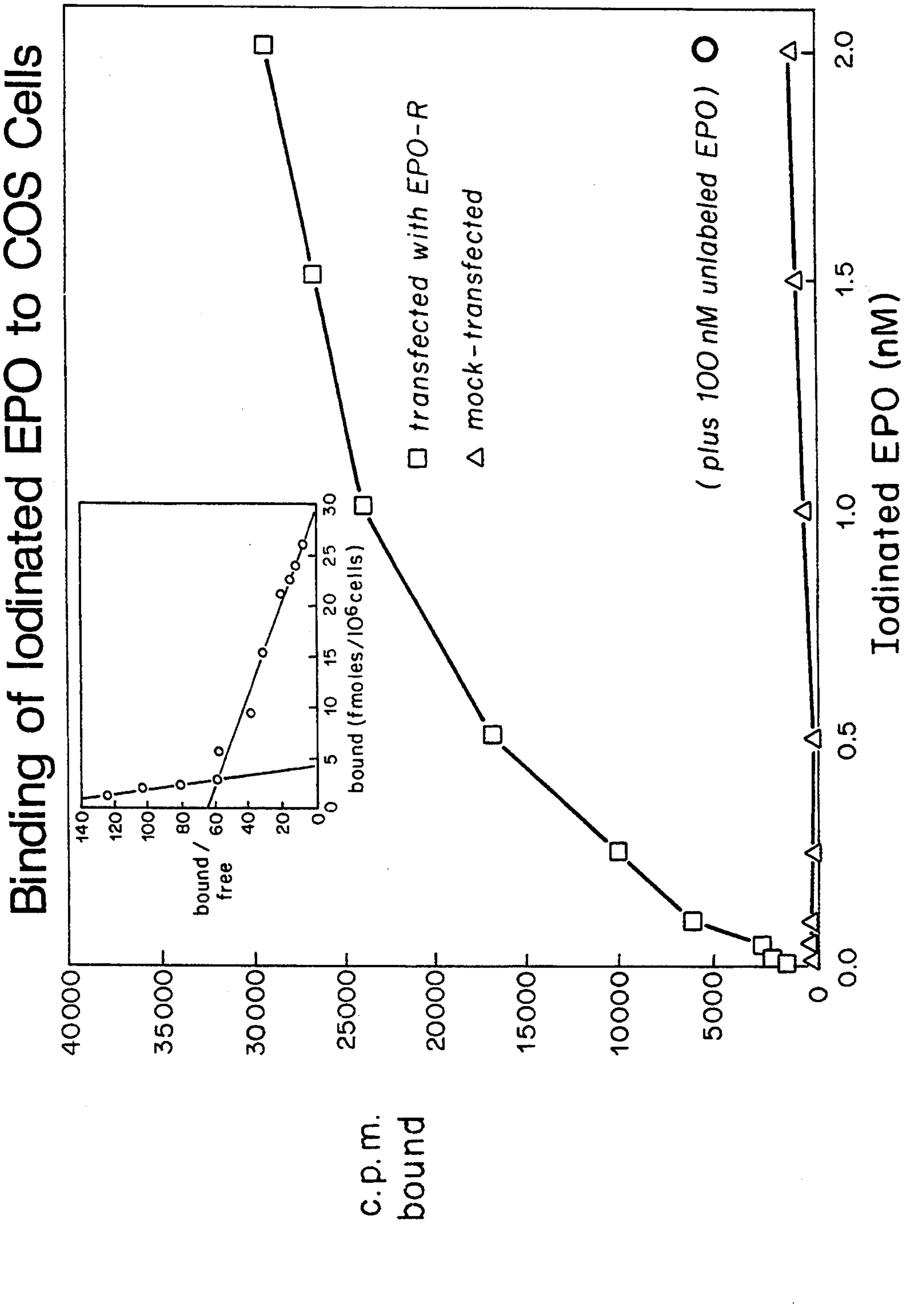
FIG. 5 is a saturation curve showing the binding of iodinated EPO to cells expressing recombinant EPO-receptors. COS-EPO-R transfectants were incubated with various concentrations of radioiodinated human EPO for eight hours at 4° C. Non-specific binding was determined by incubating radioiodinated EPO with COS-1 monolayers, mock treated with the pXM vector (without the EPO-R cDNA insert). Also, for comparison, one binding point was determined for [$^{125}$I]-EPO binding to COS EPO-R transfectants in the presence of 100 $\mu$M unlabeled EPO. The inset is a Scatchard plot of the same data.

FIGS. 4 and 5 show that the binding affinity of the recombinant murine EPO receptor, expressed in transfected COS cells, is similar to that of the receptor on MEL cells. For these experiments, MEL cells, grown as monolayers on fibronectin coated dishes, were incubated for eight hours at 4° C. with $^{125}$I EPO. Specific binding and nonspecific binding of [$^{125}$I]-EPO, measured in the presence of 100 nM unlabeled EPO was determined. Nonspecific binding was approximately half of the total (=specific plus nonspecific) binding. Because of the relatively low number of EPO-R on MEL cells and, therefore, the small specific binding observed at low concentrations of [$^{125}$I-EPO], in the 10–50 pM range, it is not possible to rule out a high affinity EPO-R in this range.

Binding was compared for COS transfectants expressing EPO-R (specific binding) versus COS cells mock-transfected with the pXM plasmid without the EPO-R cDNA insert (non-specific binding). At all EPO concentrations, specific binding was approximately 40 times the binding to mock-transfected cells. By the above criterion, over 85% of this binding is deemed specific, though the "non-specific" binding could represent low-affinity binding to the transfected EPO receptor. Scatchard analysis of the specific binding revealed the presence of two receptor species having apparent dissociation constants of two affinities, 30 pM and 210 pM, respectively. Based on immunofluorescence of COS monolayers transfected in parallel with H1 cDNA, 10% of transfected COS cells expressed recombinant surface proteins. Therefore, each COS EPO-R transfectant expressed approximately 210,000 EPO-R cell surface molecules, 16% as the high affinity class and 84% as the lower affinity class.

Attachment of radioiodinated EPO to MEL cells or other cells bearing EPO-receptors is 5–10 fold greater at 37° C. versus 4° C., suggesting that endocytosis of EPO occurs (Sawyer, S. T. et al., Proc. Natl. Acad. Sci. U.S.A. 84:3690–3694 (1987)); Mufson, R. A. and T. G. Gesner, Blood 69:1485–1490 (1987)). During cloning, the transfected cells were incubated at 37° C. while selecting clones capable of undergoing endocytosis. In COS cells expressing transfected clone 190 cDNA, cell attachment of radioiodinated EPO after 90 minutes at 37° C. was 10 times the binding to the cell surface which occurred during 8 hours at 4° C., suggesting that the recombinant EPO receptor, expressed in COS cells, will undergo endocytosis.

Antibody Inhibition of EPO Binding to Murine EPO-R

Figure 6:
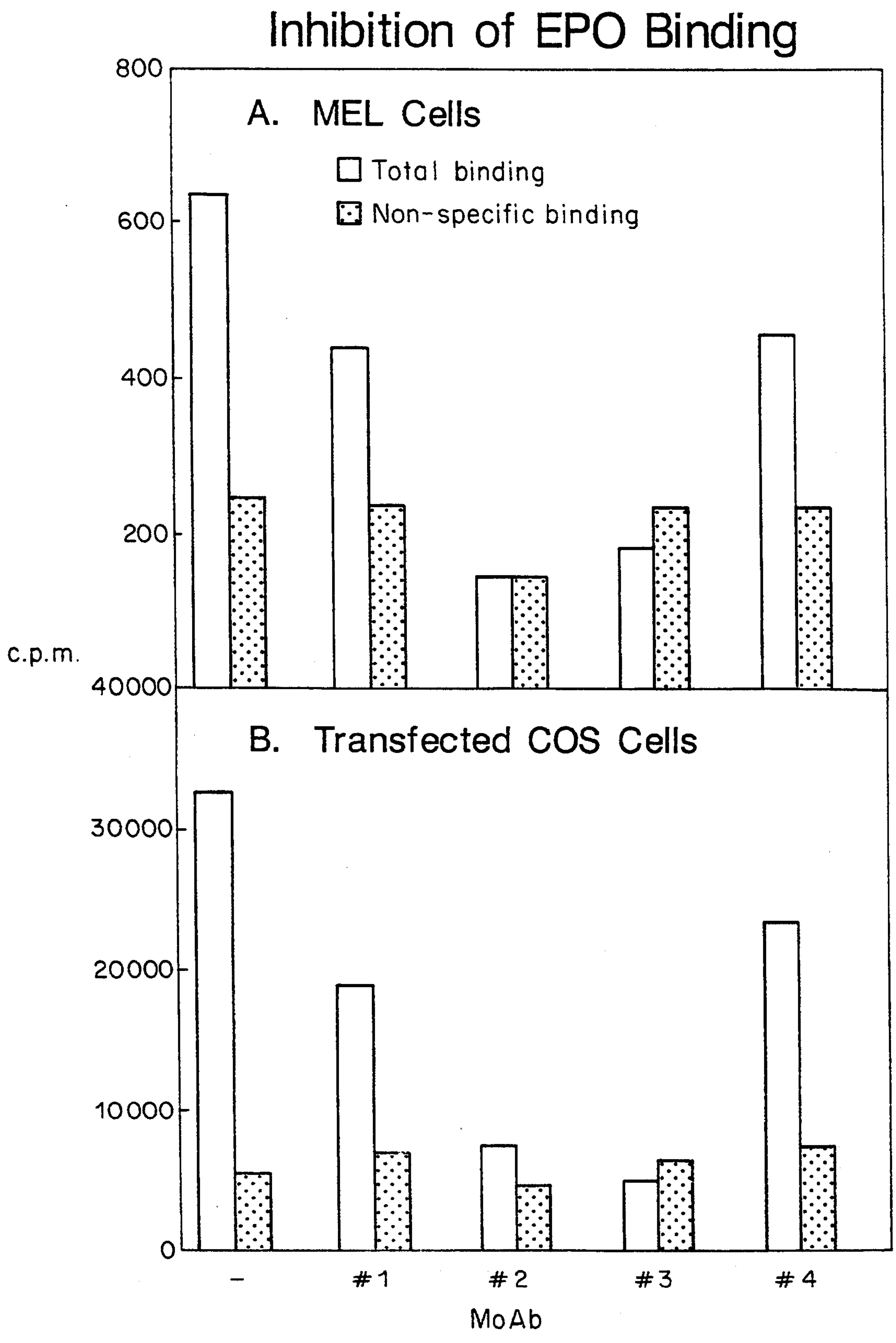
FIG. 6 is a graph showing the inhibition of EPO binding to MEL monolayers or to COS-EPO-R transfectants by monoclonal antibodies against recombinant human erythropoietin. Confluent monolayers of COS-EPO-transfectants, grown on 10 cm tissue culture dishes, were assayed 72 hours after DEAE dextran transfection. Cells were incubated with a saturating concentration [1 nM) of radioiodinated erythropoietin (100nM). After an 8 hour incubation at 4° C., monolayers were washed and specific binding versus nonspecific binding was assayed. Where indicated, radioiodinated EPO was pre-incubated with 20 nM of each of 4 monoclonal antibodies against EPO for 18 hours at 4° C. prior to the cell binding assay.

Four high affinity monoclonal antibodies against human recombinant EPO were used to determine the specificity of binding between radiolabeled EPO and the recombinant murine EPO receptor expressed in COS cells. All four monoclonal antibodies bind to EPO with $K_d$ values approximately from 0.5 nM to 50 nM. To measure the effects of these antibodies on EPO-receptor interaction, radioiodinated EPO was first incubated with enough antibody to immunoabsorb 100% of the EPO. The MEL cells were grown as monolayers on fibronectin-coated petri dishes and incubated in 4° C. with radiolabeled EPO in the presence (nonspecific binding) or absence (total binding) of unlabeled EPO. Two monoclonal antibodies (MoAb #1 and MoAb #4) did not block binding of EPO to its MEL receptor, but two others (MoAb #2 and MoAb #3) did inhibit in a dose dependent manner. This same antibody inhibition pattern was replicated by the COS transfectants (FIG. 6) suggesting that EPO binds to the recombinant murine EPO receptor with the same orientation as it binds to the EPO receptor on MEL cells.

Tissue Specific Expression of EPO-Receptor

Figure 7:
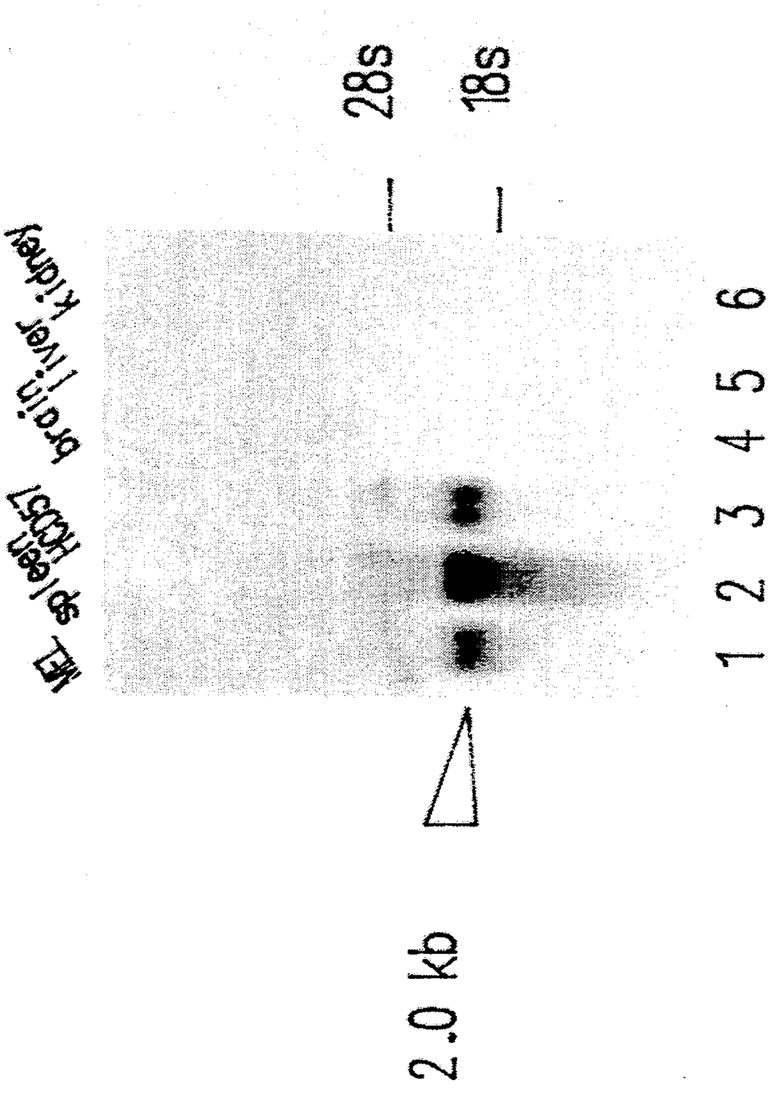
FIG. 7 is a photograph of an RNA blot analysis of EPO-R receptor mRNA. Murine erythroleukemia cell (MEL) RNA is in lane 1, murine splenic erythroblast RNA from a normal mouse treated with phenylhydrazine is in lane 2, and HCD57 RNA is in lane 3, and normal mouse brain RNA, liver RNA, or kidney RNA are in lanes 4–6, respectively. Polyadenylated RNA (2 micrograms) from the indicated cell line was loaded in each lane of a 1.2% formaldehyde-agarose gel (Maniatis et al., *Molecular Cloning: A Laboratory Manual* (1982)). After electrophoresis, the RNA was blotted onto ICN paper and the filter was probed with labeled Kpn fragment from clone 190 ($10^6$ cpm/ml). The filter was washed at 50° C. in 0.1 saline sodium citrate (SSC).
Figure 8:
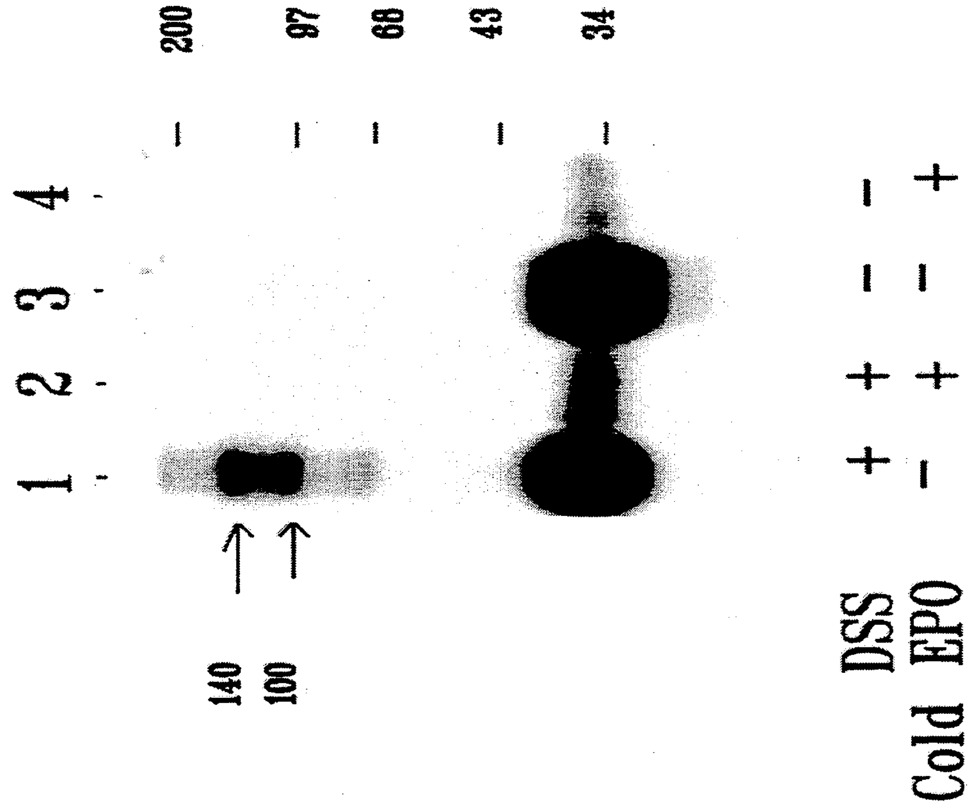
FIG. 8 is a photograph showing crosslinking of radiolabeled erythropoietin to EPO-receptor expressed in COS cells. Confluent monolayers of COS-EPO-R transfectants, grown on 10 cm tissue culture dishes, were assayed 72 hours after transfection with clone 190. Cells were incubated with 1 nM [$^{125}$I]-EPO in the absence (lanes 1,3) or presence (lanes 2,4) of 100 nM unlabeled EPO. After an 8 hour period at 4° C., monolayers were washed and again incubated at 4° C. for 1 hour in the presence (lanes 1,2) or absence (lanes 3,4) of the crosslinking agent, DSS. The material was analyzed by $NaDodSO_4$/PAGE on 10% acrylamide gels in the presence of 100 nM DTT. Size markers are in kDa.

Erythropoietin receptor transcripts were identified by Northern blot analysis of poly A selected RNA from the following cells of the erythroid lineage: MEL cells, normal splenic erythroblasts recovered from a mouse treated with phenylhydrazine, HCD57 cells, and a MEL cell line which shows absolute dependence on EPO for viability (FIG. 7). All cells contained EPO-R transcripts. The full length transcript of 2.1 kb is slightly larger than the 1.8 kb and 1.9 kb cDNA class isolated by expression cloning. Poly A selected RNA from normal mouse tissues including brain, liver, and kidney (FIG. 7, lanes 4–6 respectively) showed no hybridization with the full length $^{32}$P-labeled cDNA probe. Also, Southern blot analysis of both mouse and human genomic DNA suggests that the EPO-R transcript is most likely the product of a single gene.

The EPO receptor from MEL cells was cloned by expression. The cloning was improved by two novel features not formerly employed in other COS cell cloning strategies. First, the COS transfectants were assayed for uptake of radioiodinated EPO at 37° C., as opposed to surface binding at 4° C. This improved the signal and allowed screening of larger pools of recombinant plasmids (approximately 1000) per transfection. Secondly, the low level of nonspecific binding of radioiodinated EPO to COS transfectants and the small standard deviation from one negative pool to the next (800±134 cpm) allowed the identification of two positive plasmid pools with the use of a gamma counter alone. In contrast, for radioiodinated ligands with higher nonspecific binding, identification of a positive pool requires autoradiography (Sims, J. E. et al., Science 241:585–589 (1989)).

Although the EPO-receptor cDNA cloned encodes a single polypeptide, the COS transfectants demonstrate a high and a low affinity receptor. The generation of two affinity states by a single receptor polypeptide can be explained in multiple ways. First, the EPO-R polypeptide may undergo differential carbohydrate processing, generating two different products with different affinities. Second, the EPO-receptor may undergo phosphorylation of the cytoplasmic domain, generating two receptor affinities. Phosphorylation of the EGF-receptor, for example, is known to decrease the binding affinity for EGF. Third, the EPO-receptor polypeptide may interact with some endogenous COS cell polypeptide which is absent in MEL cells, thus generating two distinct affinities. The interaction of two discrete polypeptides to generate a high affinity receptor in some cell lines has been described for the IL-2 receptor. Fourth, the EPO polypeptide may undergo dimerization, generating a distinct affinity for both the monomeric and dimeric forms. This is appealing because the crosslinked complex of an EPO-R polypeptide dimer EPO would sum to approximately 140 kb, the size of the crosslinked complex for both normal erythroid cells (Sawyer, S. T. et al., Proc. Natl. Acad. Sci. U.S.A. 84:3690–3694 (1987)) and for EPO-R COS transfectants.

Several lines of evidence suggest that the high affinity EPO receptor is the physiologically important receptor. First, mouse splenic erythroblasts which are responsive to EPO have both high and low affinity receptors, while EPO-unresponsive MEL cells have only the low affinity receptor. Second, the dissociation constant of the high affinity receptor (50 pM) correlates well with the typical concentration of erythropoietin in mouse and human serum, suggesting that occupancy of the high affinity receptor is all that is required for signal transduction. Third, treatment of purified mouse CFU-E's with EPO results in a selective decrease of the high affinity receptor only.

Importantly, MEL cells, although expressing EPO-R's of comparable number and affinity to normal erythroblasts, do not respond to EPO by either proliferation or differentiation. MEL cells are derived from mice infected with Friend virus complex which is comprised of both the Friend leukemia virus and the replication incompetent spleen focus forming unit (SFFUp). The transformation by Friend virus complex may bypass the EPO receptor signal transduction pathway. The envelope protein encoded by the SFFUp may interact with the EPO receptor signal transduction pathway. The envelope protein encoded by the SFFUp may interact with the EPO receptor, generating constitutive signal transduction in the absence of EPO. Alternatively, but less likely, the MEL EPO-R may have undergone a mutation during MEL cell generation rendering it able to transduce a growth-promoting signal even in the absence of EPO.

EXAMPLE 1

Cloning of Murine EPO-R Gene

Cells and Cell Structure

Mouse erythroleukemia (MEL) cells, subclone 745, were obtained (Patel, V. P. and Lodish, H. F., J. Cell Biol. 102:449–456 (1986)). The cells were cultured in suspension in Dulbecco's modified Eagle's medium (DMEM) plus 13% heat-inactivated (HI)FCS in a humid $CO_2$ (5% $CO_2$ and 95% air) incubator at 37° C. For monolayer growth, MEL cells were attached to 60 mm petri dishes precoated with fibronectin (Patel, V. P. and Lodish, H. F., J. Cell Biol. 105:3105–3118 (1987)). COS-1 cells were routinely maintained in DMEM plus 10% HIFCS in a humid $CO_2$ (10% $CO_2$ and 90% air) incubator at 37° C.

Construction of pXM cDNA Library

One milligram of total RNA, prepared from uninduced MEL cells grown in suspension, was isolated by the guanidinium isothiocyanate procedure (Chirgwin et al., Biochemistry 18:5294–5299 (1979)). Five micrograms poly A selected mRNA was converted to double-stranded cDNA as described previously (Wong et al., Science 228:810–815 (1985)). Blunt end cDNA was ligated to semi-Xho adapters, non-ligated adapters were removed by CL-4B sepharose chromatography, and semi-Xho adapted cDNA was ligated into the COS-1 cell expression vector pXM, prepared as described (Yang et al., Cell 47:3–10 (1986)).

DNA Preparation

Approximately 200,000 bacterial colonies from the library were replicated onto nitrocellulose filters, plated at a density of approximately 1000 colonies per plate. Nitrocellulose replicas of each pool of 1000 colonies were made, incubated on LB plates with 5% glycerol for 30 minutes at 37° C. and stored at −80° C. The master filter from each pool was grown over 24 hours and bacterial colonies were scraped into L broth. Plasmid DNAs were isolated by a modification of the alkaline lysis techniques (Maniatis, T. et al., *Molecular Cloning: A Laboratory Manual* (1982).

COS-1 Cell Transfection

Two to five micrograms of each plasmid pool was used to transfect each of two COS-1 monolayers grown on 10 cm tissue culture dishes. Transfection was by a DEAE-dextran protocol modified by a 0.1 mM chloroquine treatment (Sompayrac and Danna, PNAS 78:7575–7578 (1981); Luthman and Magnusson, Nucl. Acids Res. 11:1295–1308 (1983)). After 72 hours, media was removed from the transfected COS-1 cells, and transfected monolayers were assayed for radioiodinated EPO binding.

Radioiodination of Recombinant Human Erythropoietin

Highly purified recombinant human erythropoietin was stored at −80° C. in a 5.8 mM $PO_4$, 0.4M NaCl, pH 7.3 buffer at 0.985 mg/ml, as determined by amino acid analysis. EPO was radioiodinated by Bilheimer's modification (Bilheimer et al., 1972) of the iodine monochloride technique of MacFarlane (MacFarlane, 1958) in the presence of Na $^{125}I$ (Amersham). Specific activities ranged from 500 to 1000 cpm per fmole.

Screening of COS-1 Transfectants

Duplicate monolayers of COS-1 transfectants, grown on 10 cm tissue culture dishes were assayed by uptake of radioiodinated EPO. Monolayers were washed three times with Hanks Balanced Salts Solution containing 25 mM Hepes, pH=7.5 (HBS/Hepes) at 23° C. Radioiodinated EPO was added to each dish in ligand binding buffer (LBB) which was 1×DME, 1% bovine serum albumin, 25 mM Hepes, pH=7.5 and $2\times10^6$ cpm $^{125}I$-EPO in 3 milliliters LBB. Monolayers were incubated for 90 minutes at 37° C. with gentle rocking. Unbound radioiodinated EPO was removed and monolayers were washed three times with HBS/Hepes at 23° C. Each monolayer was then solubilized in three milliliters of 1N NaOH and counted using an AUTO-GAMMA 500 c/800 c gamma counter (Packard). For monolayers transfected with negative pools of plasmids, background binding of radioiodinated erythropoietin was 800±134 cpm. Two positive pools were identified which yielded COS-1 monolayer binding of approximately 1200 cpm. After identification of a positive pool, a frozen replica on nitrocellulose, containing approximately 1000 colonies, was thawed and cut into approximately 30 sections. Minipreps were prepared from individual sections and transfected into COS cells. Individual colonies were next picked from the positive sections. After a final round of miniprep and COS transfection, clone 190 was recovered.

Erythropoietin Surface Binding Assay

Confluent monolayers of MEL cells, grown in 60 mm bacteriophage petri dishes pre-coated with fibronectin, were prepared (Patel and Lodish, supra (1987)). Confluent monolayers of COS-1 cells, transfected by the DEAE dextran method 72 hours before the binding assay with either two micrograms of clone 190 cDNA in pXM or two micrograms of pXM without cDNA insert (mock-transfected) per monolayer, were prepared. Monolayers were washed at 4° C. with HBS/Hepes three times. Radioiodinated EPO (10 pM to 2 nM range) was added to each monolayer in LBB. Incubations were performed at 4° C. for eight hours with gentle rocking. Monolayers were washed, solubilized, and counted in the gamma counter as described. Assays for nonspecific binding were performed in which the assay mixture contained a 100-fold excess 1(100 nM) of unlabeled erythropoietin. The radioactivity bound in the assays with excess unlabeled erythropoietin (nonspecific binding) was subtracted from the total binding to yield the specific binding. All binding assays were run in duplicate.

Calculation of Transfection Efficiency

Two micrograms of a plasmid clone, containing the cDNA encoding the Hi subunit of the human asialoglycoprotein receptor in the vector, pXM, was transfected into COS-1 monolayers. After 72 hours, at the time of peak heterologous protein expression, COS transfectants were labeled sequentially with an anti-peptide antibody against the carboxy terminus of H1 (Bischoff and Lodish, J. Biol. Chem. 262:11825–11832 (1987)) followed by a fluorescein conjugated goat anti-rabbit antibody. The percent of transfected cells was determined using a fluorescent microscope.

Hybridization Techniques

Southern and Northern blot hybridizations were performed according to standard techniques described elsewhere (Maniatis et al., *Molecular Cloning: A Labora-*

*tory Manual* (1982)). A cDNA probe was prepared from the full length Kpn fragment of clone 190 by the random oligonucleotide primer labeling method (Feinberg and Vogelstein, Anal. Biochem. 132:6–13 (1983)).

EXAMPLE 2

Cloning of Human EPO-R Gene

Isolation of the Human Gene for an Erythropoietin Receptor pMuEPO-R190 is plasmid pXM containing a 1.8 kb murine cDNA fragment encoding an erythropoietin receptor. This cDNA fragment was excised from plasmid pMuEPO-R190 by the restriction enzyme Kpn1. Using this DNA fragment as a probe, it was possible to isolate the human gene for the erythropoietin receptor. Analysis of the mouse genomic DNA that had been subjected to different restriction enzyme treatment (e.g., BamHI, EcoRI, EcorRI, HindIII) revealed there was a single gene for the erythropoietin receptor per haploid genome. In the human genomic DNA, fainter bands above a nonspecific background were detected. Therefore, the human gene for an erythropoietin receptor was identified by using the murine erythropoietin receptor cDNA as a probe.

A commercially available human genomic library in phage Lambda Dash human genomic library was screened for the human erythropoietin receptor gene by infecting *E. coli* strain LE392 with $6\times10^5$ pfu and plating the infected cells on 15 cm NZCYM agar plates at a density of $1.5\times10^4$ pfu per plate. These phages were screened in duplicate using the procedure of Benton and Davis (*Molecular Cloning: A Laboratory Manual* (1982)) with the 1.8 kb murine erythropoietin receptor cDNA fragment excised by KpnI digestion from pMuEPO-R190. The 1.8 kb murine erythropoietin receptor cDNA fragment was radiolabeled as described above. The human genomic library was screened using the standard hybridization mixture (above) at 48° C. for 18 hours. The nonspecific hybridization signals are removed by washing the filters at 55° C. in 0.5×SSC for 1 hour.

Phages exhibiting a strong hybridization signal were picked and replated at about 100 pfu per 10 cm NZCYM, plate, and screened in duplicate again by the Benton and Davis procedure using the murine erythropoietin receptor cDNA fragments as a probe.

Two independent phages huEPOR-2-la and huEPOR-3-2 were isolated. Phage DNA was prepared from each, by methods described in Maniatis, et al., *Molecular Cloning: A Laboratory Manual* (1982). Phage DNA was then treated with restriction enzyme BamHI, phenol extracted and coprecipitated with M13mp8 DNA restricted with BamHI and treated with calf alkaline phosphatase. The precipitated DNA was pelleted by centrifugation and redissolved in 50 μl of ligase buffer containing T4 DNA ligase and incubated for 3 hours at 16° C. 5 μl of this reaction mixture was used to transform *E. coli* strain JM101/TG1. The plaques were screened using the Benton and Davis procedure and probed with the 1.8 kb murine erythropoietin receptor cDNA fragment. Phage plaques exhibiting hybridization were isolated and single stranded phage DNA was prepared for use as a DNA sequencing template. The sequence of each recombinant M13 phage's genomic human DNA fragment was determined by the dideoxy chain termination technique described by Sanger, et al., PNAS 74:5463–5467 (1977). Commercially available primers were used which flanked the human genomic DNA insertion site in M13. Based on the internal sequence further primers were synthesized to sequence the whole of the inserted DNA.

Genomic DNA Sequence and Characterization

The gene appears to be approximately 6 kb in length and is covered by four BamHI fragments of 1.02 kb, 1.6 kb, 4.37 kb and 0.5 kb. It appears to contain all the coding sequence based on similarity to the murine and identity with human cDNA clones (see below).

The gene contains eight exons (FIGS. 9 and 9A open triangles) where the first five exons encode the extracellular domain, the sixth the transmembrane region and the last two the cytoplasmic tail of the receptor.

The 5′ -noncoding region which is expected to contain regulatory sequences for controlling transcription is shown in FIG. 10. There appears to be no canonical CAAT or TATA sequences in this region. Rather there is one Sp1 binding site (CGCCC), a site for the erythroid-specific transcription factor, GF-1 (TTATCT) and a motif (CACCC) found in the promotor regions of globin genes. (FIG. 10)

Isolation of the Human cDNA Gene for an Erythropoietin Receptor

The human cDNA gene for the erythropoietin receptor can be isolated from a cDNA library of mRNA from a human tissue or cell line. Examples of human tissues which may express the human erythropoietin receptor are fetal spleen, fetal liver, bone marrow, erythroleukemia cells, and established erythroleukemia cell lines such as OCIM1 (Broudy, et al., PNAS 85:6513–6517 (1988)); HEL (Martin and Papayannopoulou, Science 216:1233–1235 (1982)); KMOE (Kaku, et al., Blood 64:314–317 (1980)); K562 (Andersson, et al., Nature 278:364–365 (1979)) and JK-1 (Hitomi, et al., BBRC 154:902–909 (1988)).

mRNA was prepared from the tissue or cell line source by standard techniques and enriched for mRNA by chromatography on oligo (dT) cellulose. The isolated mRNA was subjected to electrophoresis through an agarose gel containing formaldehyde (Maniatis, et al., *Molecular Cloning: A Laboratory Manual* (1982)) and the mRNA was transferred to nitrocellulose. The nitrocellulose filter was hybridized with the murine erythropoietin receptor cDNA fragment. The erythropoietin receptor cDNA fragment was radiolabeled to a specific activity of $10^8$dpm/μg of DNA. The hybridization was conducted at 48° C. for 18 hours. The filter was washed at 55° C., 0.5×SSC for 1 hour, and then autoradiographed. The human erythroleukemia line, OCIM1, was found to express a 2 kb transcript which hybridized with the murine EPO receptor fragment.

A cDNA library was prepared, as described above for the isolation of the murine EPO receptor cDNA, in the expression plasmid pMT21, beginning with five μg of poly-A selected RNA from OCIM1 cells. pMT21 was derived from pMT2 (Kaufman, R. J. et al., Mol. Cell. Biol. 9:946–958 (1989)) through the following two modifications. First, 76 bp of the 5′ untranslated region of the DHFR cDNA including a stretch of 19 G residues from G/C tailing for cDNA cloning was deleted. In this process, a XhoI site was inserted to obtain the following sequence immediately upstream from

DHFR:

-continued

5′-CTGCAGGCGAGCCTGAATTCCTCGAGCCATCATG-3′

PstI Eco RI XhoI

Then, 250 bp was deleted from the adenovirus VA region by digestion with EcoRV and XbaI, treatment with Klenow fragment of DNA polymerase I, and ligation to a ClaI linker (CATCGATG). A total of 180,000 clones were screened by hybridization using the radiolabeled KpnI fragment containing the murine erythropoietin gene sequence. Eight positive clones were detected; two clones, #18 and #27, were sequenced as described for the murine clone.

Based on the sequence obtained from the open reading frame of clone #18 two oligonucleotides were synthesized (G G G A A T T C A T G G A C C A C C T C G G G G C G T C C C T C and GGGAATTCCTAAGAGCAAGCCACATAGCTGGG), which also contained EcoRI restriction sites for subsequent cloning, and used to amplify, by the polymerase chain reaction (Perkin-Elmer, Norwalk, Conn.), the human EPO receptor gene from fetal liver genomic DNA (Toole, J. J., et al., Nature 312:342 (1984)). The primers were annealed at 50° C. and extended for 5 minutes, and this process was repeated for 40 cycles.

Characterization and Sequence of the Human cDNA

The nucleotide sequence of Clone #18 contains a single open reading frame of 1,524 nucleotides encoding a 508 amino acid protein with a calculated molecular mass of 55 kDa. Clone #18 also contained the intron between exons seven and eight at nucleotides 914/5 (FIG. 9A) based on a comparison to the genomic clone. Clone #27 was identical to clone #18 except it was incomplete at the 5′- and 3′- ends of the gene and it did not contain the intron. The clone from fetal liver cDNA was identical to the coding sequence of clone #18, except for a single T→A difference at nucleotide 235 (FIG. 9), and it did not contain the intron sequence.

The cDNA and protein sequence of the human EPO receptor were both 82% similar to the murine EPO receptor. The main structural features, discussed above for the murine receptor, are conserved for the human, except for an amino acid insertion between amino acids 71 and 76 and the absence of a N-linked glycosylation site in the cytoplasmic domain in the human receptor.

EXAMPLE 3

Mammalian Cell Expression and Binding Characteristics of the Human EPO Receptor The gene for the EPO receptor may be expressed either transiently in COS cells or as stable cell lines in CHO cells using a selectable marker gene, coexpressed with the receptor, which allows the amplification of the integrated gene.

The region containing the intron sequence in clone #18 was substituted with the corresponding region of clone #27, yielding a contiguous coding sequence for the human EPO reporter in the mammalian expression plasmid, pMT21 (described in Example 2). The expression plasmid was denoted as P18R3′.

Stable CHO lines expressing the human EPO receptor were obtained by transfecting p18R3′ by the method of lipofection (BRL, Life Technologies Inc., U.S.A.) into CHO Dukx cells, followed by successive rounds of selection and amplification of the sectable marker gene, dihydrofolate reductase, in increasing concentrations of methotrexate (Kaufman, R. J. et al., Mol. Cell. Biol. 5:1750–1759 (1985)).

The expression of the human EPO receptor in COS cells transiently transfected with P18R3′ or stable CHO lines as studied by labelling the cells with [$^{35}$S]-methionine, as described (Dorner, A. J. and Kaufman, R. J., Methods in Enzymology 185:577–596 (1990)), for 15 to 60 minutes. Cell extracts after lysis were immunoprecipitated using a rabbit polyclonal antibody to a peptide based on the amino terminal sequence of the murine EPO receptor (Li, J., et al., Nature 343:762 (1990)). Examination of the immunoprecipitates on a 10% SDS-PAGE revealed one major band at approximately 65 kDa.

The level of cell surface expression of the human EPO receptor was determined by the erythropoietin surface binding assay, described above for the expression of the murine EPO receptor in COS-1 cells, except that radioiodinated EPO, from 10 pM to 2 nM, was bound for one hour at 37° C. in the presence of 0.02% (w/v) sodium azide and 1% (v/v) aprotinin. For example, one CHO cell line, 9′.250, cultured in media containing 0.25 μM methotrexate, had approximately 105,000 EPO binding sites per cell, of which 34% had an affinity of 126 pM and the remainder an affinity of 660 pM for EPO, based on Scatchard analysis of the binding data (Scatchard, G., Ann. N.Y. Acad. Sci. 51:660–671 (1948)). Another cell line 10′.1.25 cultured in media containing 1.25 μM methotrexate, had approximately 770,000 EPO binding sites per cell exhibiting a single affinity of 3 nM.

The EPO binding sites on the CHO cell line, 9′.250, were further characterized by crosslinking bound radioiodinated EPO to the receptor with disuccinimidyl suberate, with the modifications described above for the determination of the amount of cell surface binding of EPO. Examination of the material by polyacrylamide gel electrophoresis, in the presence of sodium dodecylsulfate, under reducing conditions revealed two complexes of apparent molecular mass of 105 and 140 kDa.

Biological Activity of the Human EPO Receptor

The murine IL-3 dependent cell lines, 32D (Hapel, A. J. et al., Blood 64:786–790 (1984)) and FDCP1 (Dexter, T. M., et al., J. Exp. Med. 152:1036–1047 (1980)) ($1\times10^7$ cells), were transfected, by electroporation, (D'Andrea, A. D. et al., Blood 75:874 (1990)) with 0.1 to 0.2 mg of p18R3′ linearized with the restriction enzymes NdeI and ClaI, respectively. The cells were grown in IL-3 containing media for two days then moved to media containing EPO at 1 u/ml. After approximately 10 to 14 days viable cells appeared. The EPO-dependent cell lines are known as 32DE and FDCPE.

The FDCPE and 32DE cell lines were further characterized by their dose dependent response to EPO. A 96 well plate was seeded with $1\times10^4$ cells/well and incubated with EPO (0.0001 to 10 u/ml) for 24 hours and then labelled with [$^3$H]-thymidine for 4 hr, the cells were collected and counted for thymidine incorporation. The cells respond to EPO dose dependent manner from 0.01 to 1 u/ml.

EXAMPLE 4

A Secreted Human Erythropoietin Receptor

A secreted form of the human erythropoietin receptor was prepared by expression of a modified DNA where the regions encoding the cytoplasmic and transmembrane domains were deleted and/or a stop codon was introduced 3' to the codon for the amino acid at the carboxy terminus of the extracellular domain.

Single stranded DNA was generated from the fetal liver cDNA clone ligated into M13mp19 at the EcoRI site (see above). The codon encoding the first amino acid of the transmembrane (FIG. 9A) was changed to a stop codon (TAG) by site-directed mutagenesis by the method of Zoller and Smith, as adapted by Eckstein using the system devised by Amersham International, U.K., with the oligonucleotide, CTAGCGACCT-GGACCCCTAGGTCCTGACGCTCTCCCTC, where the stop codon is underlined. The Rf form of the M13 derivative containing the mutation was digested with BglII (the BglII cohesive ends of the DNA were removed with the Klenow fragment of DNA Polymerase I), followed by XhoI. These restriction sites are approximately 90 bp 3' and 500 bp 5' to the stop codon, respectively, and the 595 bp fragment was isolated. Also the 1.6 kb fragment of the expression plasmid, pED, was generated by digestion with SalI (the SalI cohesive ends of the DNA were removed with the Klenow fragment) and ClaI. pED was derived as follows: pMT2-ECAT1 (Jang, S. K. et al., J. Virol. 63:1651–1660 (1989)), was digested with Eco RI and PstI resulting in a 2752 bp fragment. This fragment was digested with TaqI yielding an Eco RI-TaqI fragment of 508 bp which was purified by electrophoresis on low melting agarose gel. A 68 bp adapter was synthesized with a 5' TaqI protruding end and a 3' XhoI protruding end which has the sequence:

5'TCGAGGTTAAAAAACGTCTAGGCCCCCCGAACCACGGGGACGTGGTTTTCCTTT
TaqI
GAAAAACACGATTGCTCGAG-3'
XhoI

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulted in the vector pED4. The resulting plasmid has the authentic DHFR ATG 15 bp downstream from ATG-10 of the EMC virus. pED was derived from pED4 by insertion of the polylinker having the sequence 5'-TGCAGGTCGACT-CTAGACCCGGGAATT-3' between the PstI and Eco RI sites.

The 595 bp fragment and pED were ligated together in the presence of the 4.1 kb fragment of p18R3' prepared by digesting with ClaI and XhoI to yield the expression plasmid, psEPOR. The secreted form of the EPO receptor is encoded by nucleotides −70 to 845 of FIGS. 9 and 9A.

Mammalian Cell Expression and Binding Characteristics of the Secreted Human EPO Receptor The expression of the secreted form of the human EPO receptor was studied by transient transfection of COS cells with psEPOR. The transfected cells were metabolically labelled with 0.2 mCi of [$^{35}$S]-methionine for 30 minutes followed by a 'chase' period with unlabelled amino acids of 30 minutes to 22 hours. Media and cell extracts after lysis were immunoprecipitated as described above. Examination of the immunoprecipitates on 12% SDS-PAGE revealed two major bands of 27 and 29 kDa in the cell extract which decreased in intensity to background levels by 3 hours after labelling. Conversely immunoprecipitates from media demonstrated a single band of 32 kDa, which increased in intensity to a maximum level by 3 hours.

To further characterize the secreted receptor, COS conditioned media (0.2 ml) was incubated at 4° C. for 18 hours with radioiodinated EPO (3000 Ci/mmole, 0.4 pmoles) in the presence or absence of a 50-fold excess of unlabelled EPO. The bound EPO was crosslinked to the receptor by incubation with disuccinimidyl suberate and the crosslinked mixture were treated with the rabbit polyclonal antibody to the murine EPO receptor, as previously described. Examination of the immunoprecipitates on a 10% SDS-PAGE revealed a band at 72 kDa (32 kDa for the secreted receptor plus 40 kDa for the radioiodinated EPO), which was not present in the reactions with excess unlabelled EPO.

Stable CHO lines expressing the secreted form of the human EPO receptor were obtained by transfecting CHO Dukx cells with psEPOR followed by selection in media containing increasing levels of methotrexate, as described above for the expression of the full-length receptor. The level of secreted protein was assessed by comparing its relative intensity of staining with Coomassie Brilliant Blue to known amounts of molecular weight standards after SDS-polyacrylamide gel electrophoresis. Relative expression levels between CHO lines was examined by the method of 'Western' blotting using the rabbit anti-murine EPO receptor polyclonal antisera discussed above. Generally, lines cultured in media containing 3.125 and 15.6 μm methotrexate secreted the receptor to a level of 1–2 μg/ml over a 24 hr period from $5\times10^6$ cells.

Inhibition of EPO Binding to FDCPE Cells by Secreted EPO Receptor

FDCPE cells were incubated and assayed with either 0.4, 0.8 and 1 u/ml of EPO as described above but also with serial dilutions of media from a CHO line expressing the secreted EPO receptor (ca. 0.5 μg/ml). The conditioned media inhibited the incorporation of [$^3$H]-thymidine into the FDCPE cells, and this effect declined in a dose dependent manner as the conditioned media was diluted.

Purification of the Secreted Form of the Human EPO Receptor

Conditioned media was collected over 24 hr periods from CHO cell lines expressing the secreted EPO receptor at a level of 0.5–2 μg/ml, under serum-free conditions in the presence of the protease inhibitor aprotinin (1:100 v/v). The conditioned media was filtered through a 0.2μ filter and stored at −80° C.

The conditioned media was concentrated 25–50 fold using an Amicon stirred cell with a YM-10 Diaflo filter. The concentrate was made 30% in ammonium sulfate (w/v), the supernatant was collected by centrifugation and ammonium sulfate was added to the supernatant to a final concentration of 55% (w/v). The 55% pellet was collected by centrifugation and back-extracted twice with 1/10 of the original concentrate volume of 35% ammonium sulfate.

The 35% extractions containing the secreted receptor were purified by hydrophobic interaction chromatography on a phenylsepharose column developed in 35% ammonium sulfate, 25 mM Hepes pH 7.5, followed by a gradient from 35% to 0% ammonium sulfate, 25 mM Hepes pH 7.5. Alternatively, the 35% extractions were extensively dialyzed against 5 mM Tris-HCl pH 7.5. The dialysate containing the secreted EPO receptor was further purified by ion-exchange chromatography on Q-Toyapearl or Mono-Q column developed with 25 mM Hepes pH 7.5, followed by a gradient of 0M to 1M NaCl, 25 mM Hepes pH 7.5.

Fractions containing the secreted EPO receptor, by SDS polyacrylamide gel electrophoresis and by immunoblot using the antibody described above, were pooled. The combined fractions from either chromatography procedure were purified by size exclusion chromatography on a Biosil TSK-250 column developed in phosphate buffered saline, yielding the secreted EPO receptor in 70–80% purity.

The secreted receptor may be obtained in purity in excess of 95% by one or a combination of the following chromatographic steps. First, by affinity purification using; blue sepharose, wheat germ lectin, lentil lectin or by EPO linked to a suitable matrix, such as sepharose. Alternatively, a size exclusion matrix can be used which has a greater resolving power than the one described above. Finally, a reversed phase matrix, e.g. silica linked to $C_{18}$, $C_8$ or $C_4$ hydrocarbon side chains or a hydroxylapatite matrix may be more suitable to obtain the desired level of purity. The complete human and murine receptors may be similarly purified.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. An isolated polypeptide encoded by a DNA selected from the group consisting of:

(i) a DNA comprising the DNA sequence set forth in FIGS. 2 and 2A;

(ii) the DNA insert in plasmid pXM having ATCC No. 40546;

(iii) a DNA capable of hybridizing under stringent conditions to the DNAs of (i) and (ii); and (iv) a DNA differing from the DNAs of (i)–(iii) in codon sequence due to the degeneracy of the genetic code;

said polypeptide having the ability to specifically bind to erythropoietin.

2. An isolated polypeptide encoded by a DNA selected from the group consisting of:

(i) a DNA comprising the DNA sequence set forth in FIGS. 9 and 9A;

(ii) the DNA insert in lambda phage vector having ATCC No. 40547;

(iii) the DNA insert in lambda phage vector having ATCC No. 40548;

(iv) a DNA capable of hybridizing under stringent conditions to the DNAs of (i)–(iii); and (v) a DNA differing from the DNAs of (i)–(iv) in codon sequence due to the degeneracy of the genetic code;

said polypeptide having the ability to specifically bind to erythropoietin.

3. An isolated polypeptide encoded by a DNA selected from the group consisting of:

(i) a DNA comprising the DNA sequence of FIGS. 9 an 9A from nucleotide −70 to nucleotide 845;

(ii) a DNA capable of hybridizing under stringent conditions to the DNA of (i); and (iii) a DNA differing from the DNAs of (i) and (ii) in codon sequence flue to the degeneracy of the genetic code;

said polypeptide having the ability to specifically bind to erythropoietin and to be secreted into a culture medium.

* * * * *